United States Patent
Ebright et al.

(10) Patent No.: US 12,209,082 B2
(45) Date of Patent: Jan. 28, 2025

(54) ANTIBACTERIAL AGENTS: SOLUBLE SALTS AND AQUEOUS FORMULATIONS OF PYRONINS

(71) Applicant: Rutgers, the State University of New Jersey, New Brunswick, NJ (US)

(72) Inventors: Richard H. Ebright, New Brunswick, NJ (US); Yon W. Ebright, New Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 827 days.

(21) Appl. No.: 16/969,529

(22) PCT Filed: Feb. 12, 2019

(86) PCT No.: PCT/US2019/017700
§ 371 (c)(1),
(2) Date: Aug. 12, 2020

(87) PCT Pub. No.: WO2019/160875
PCT Pub. Date: Aug. 22, 2019

(65) Prior Publication Data
US 2021/0002266 A1    Jan. 7, 2021

Related U.S. Application Data

(60) Provisional application No. 62/630,117, filed on Feb. 13, 2018.

(51) Int. Cl.
*C07D 417/06* (2006.01)
*A01N 47/12* (2006.01)
(Continued)

(52) U.S. Cl.
CPC ........... *C07D 417/06* (2013.01); *A01N 47/12* (2013.01); *A61K 9/0019* (2013.01); *A61P 31/04* (2018.01);
(Continued)

(58) Field of Classification Search
CPC ..... C07D 417/06; A61K 9/0019; A61P 31/04; A61P 31/06
See application file for complete search history.

(56) References Cited

U.S. PATENT DOCUMENTS 4,061,769 A   12/1977  Ohno et al.
4,421,763 A   12/1983  Hamano et al.
(Continued)

FOREIGN PATENT DOCUMENTS

WO    2007094799    8/2007
WO    2012033846    3/2012
(Continued)

OTHER PUBLICATIONS

Berge et al. J. Pharm. Sci., 1977, 66 (1), 1-19.*
(Continued)

*Primary Examiner* — Alicia L Otton
(74) *Attorney, Agent, or Firm* — Viksnins Harris Padys Malen LLP

(57) ABSTRACT

The invention provides salts of formula Ia, Ib, Ic, or Id: wherein variables are as described in the specification, as well as compositions comprising a salt of formula Ia-Id, methods of making such salts, and methods of using such salts as, e.g., inhibitors of bacterial RNA polymerase and as antibacterial agents.

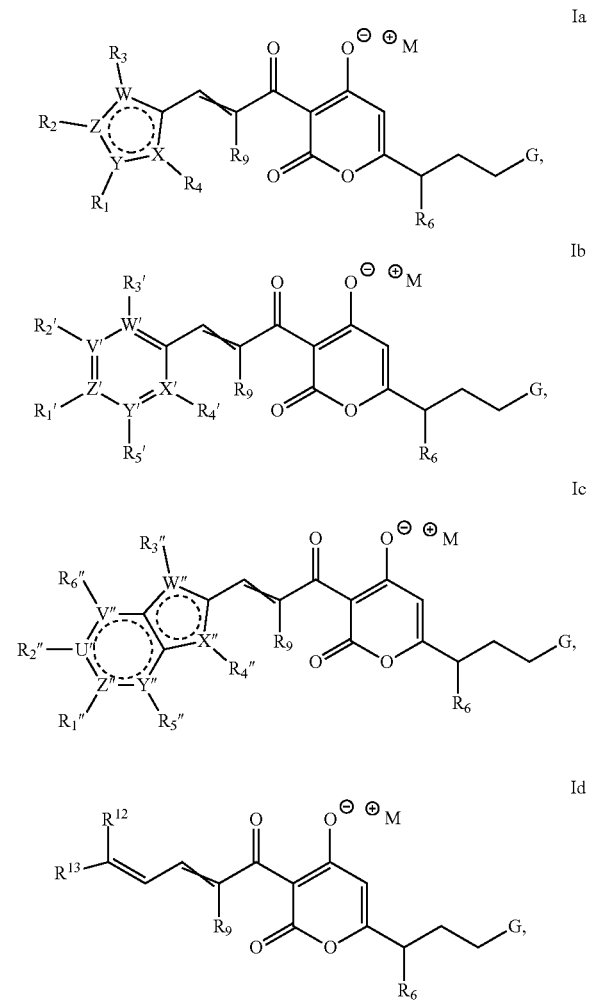

3 Claims, No Drawings

(51) Int. Cl.
*A61K 9/00* (2006.01)
*A61P 31/04* (2006.01)
*A61P 31/06* (2006.01)

(52) U.S. Cl.
CPC .......... *A61P 31/06* (2018.01); *C07B 2200/05* (2013.01); *C07B 2200/07* (2013.01)

(56) References Cited

U.S. PATENT DOCUMENTS

| | | | |
|---|---|---|---|
| 6,022,983 | A | 2/2000 | Wuonola et al. |
| 6,169,181 | B1 | 1/2001 | Romines et al. |
| 6,191,288 | B1 | 2/2001 | Ramamoorthy |
| 6,228,882 | B1 | 5/2001 | Wuonola et al. |
| 8,114,583 | B2 | 2/2012 | Ebright et al. |
| 8,772,332 | B2 | 7/2014 | Ebright et al. |
| 9,133,155 | B2 | 9/2015 | Ebright et al. |
| 9,187,446 | B2 | 11/2015 | Ebright et al. |
| 9,315,494 | B2 | 4/2016 | Moslin et al. |
| 9,315,495 | B2 | 4/2016 | Ebright et al. |
| 9,592,221 | B2 | 3/2017 | Ebright et al. |
| 2003/0065039 | A1 | 4/2003 | Kharazmi et al. |
| 2005/0187170 | A1 | 8/2005 | Bantia et al. |
| 2006/0100291 | A1 | 5/2006 | Perry et al. |
| 2006/0246479 | A1 | 11/2006 | Ebright |
| 2007/0292355 | A1 | 12/2007 | Tamarkin et al. |
| 2013/0237595 | A1 | 9/2013 | Ebright et al. |
| 2013/0289128 | A1 | 10/2013 | Ebright et al. |
| 2013/0296421 | A1 | 11/2013 | Ebright et al. |
| 2014/0073688 | A1 | 3/2014 | Pfarr et al. |
| 2015/0011647 | A1 | 1/2015 | Ebright et al. |
| 2015/0031640 | A1 | 1/2015 | Ebright et al. |
| 2015/0051275 | A1 | 2/2015 | Ebright et al. |
| 2016/0263083 | A1 | 9/2016 | Ebright et al. |
| 2021/0002246 | A1 | 1/2021 | Ebright et al. |

FOREIGN PATENT DOCUMENTS

| | | |
|---|---|---|
| WO | 2012037508 | 3/2012 |
| WO | 2013119564 | 8/2013 |
| WO | 2013142812 | 9/2013 |
| WO | 2013192352 | 12/2013 |
| WO | 2014090875 | 6/2014 |
| WO | 2019160873 | 8/2019 |

OTHER PUBLICATIONS

Andre, et al., "Novel synthetic molecules targeting the bacterial RNA polymerase assembly", Journal of Antimicrobial Chemotherapy, 57, 245-251 (2006).

Belogurov, et al., "Transcription inactivation through local refolding of the RNA polymerase structure", Nature 457 (7227), 332-335 (2009).

Chatterjee, et al., "Isolation and structure of archangelenone. Flavonoid constituent of Angelica archangelica", XP002692911, Database Caplus [Online] Chemical Abstracts accession No. 1973:489536.

Chopra, I., "Bacterial RNA polymerase: a promising target for the discovery of new antimicrobial agents", Curr. Opin. Investig. Drugs 8, 600-607 (2007).

Darst, "New inhibitors targeting bacterial RNA polymerase", Trends Biochem. Sci. 29 (4), 159-162 (2004).

Doundoulakis, et al., "Myxopyronin B analogs as inhibitors of RNA polymerase, synthesis and biological evaluation", Bioorganic and Medicinal Chemistry Letters, vol. 14 (22), 5667-5672 (2004).

Doundoulakis, et al., "Myxopyronin B analogs as inhibitors of RNA polymerase, synthesis and biological evaluation", HCAPLUS Accession No. 2004:863124, 5 pages, Bioorganic & Medicinal Chemistry Letters, 14(22), 5667-5672 (2004).

Heron, M., et al., "Deaths: Final Data for 2006", National Vital Statistics Reports, vol. 57 (14), 135 pages (Apr. 17, 2009).

Ho, et al., "Structures of RNA polymerase-antibiotic complexes", Curr. Opin. Structl. Biol. 19, 715-723 (2009).

HU, "Total syntheses of biologically active natural products: motuporin, oleandolide, (±)-myxopyronin A and B", HCAPLUS Accession No. 2000:514322, 1 page, Diss. Abstr. Int., B 2000, 60(10), 5094.

Klevins, R, et al., "Estimating health care-associated infections and deaths in U.S. hospitals, 2002", Public Health Reports 122, 160-166 (2007).

Lira, R., et al., "Syntheses of novel myxopyronin B analogs as potential inhibitors of bacterial RNA polymerase", Bioorganic & Medicinal Chemistry Letters 17(24), 6797-6800 (2007).

Mukhopadhyay, et al., "The RNA polymerase "switch region" is a target for inhibitors", Cell 135, 295-307 (2008).

Mukhopadhyay, et al., "The RNA polymerase "switch region" is a target for inhbitiors", HCAPLUS Accession No. 2008:1312023, 2 pages, Cell 135(2), 295-307 (2008).

Patent Cooperation Treaty, International Searching Authority, Search Report and Written Opinion for PCT/US2019/017700, 12 pages, Jun. 20, 2019.

Scott, R, et al., "The Direct Medical costs of Healthcare-Associated Infections in U.S. Hospitals and the Benefits of Prevention", Public Health Reports, 122, 160-166, Center for Disease Control and Prevention, 16 pages (2009).

Srivastava, et al., "New Target for Inhibition of Bacterial RNA Polymerase: Switch Region", Curr. Opin. Microbiol. 14, 532-543 (2011).

Villain-Guillot, et al., "Progress in targeting bacterial transcription", Drug Discov. Today 12 (5/6), 200-208 (2007).

Werner, S, et al., "Synthesis of non-natural flavanones and dihydrochalcones in metabolically engineered yeast", Journal of Molecular Catalysis B: Enzymatic 66, 257-263 (2010).

World Health Organization, "The Global Burden of Disease—2004 Update", World Health Organization, Geneva, ISBN 978 92 4 156371 0, 160 pages (2008).

* cited by examiner

ANTIBACTERIAL AGENTS: SOLUBLE SALTS AND AQUEOUS FORMULATIONS OF PYRONINS

CROSS-REFERENCE TO RELATED APPLICATION(S)

This application claims priority to U.S. Provisional Application No. 62/630,117, filed Feb. 13, 2018, which is hereby incorporated by reference in its entirety.

GOVERNMENT FUNDING

This invention was made with government support under AI109713, and AI090837 awarded by the National Institutes of Health. The government has certain rights in the invention.

BACKGROUND OF THE INVENTION

Bacterial infectious diseases kill 100,000 persons each year in the US and 11 million persons each year worldwide, representing nearly a fifth of deaths each year worldwide (Heron et al., *Final Data for 2006. National Vital Statistics Reports*, Vol. 57 (Centers for Disease Control and Prevention, Atlanta GA) and World Health Organization (2008) *The Global Burden of Disease: 2004 Update* (World Health Organization, Geneva)). In the US, hospital-acquired bacterial infections strike 2 million persons each year, resulting in 90,000 deaths and an estimated $30 billion in medical costs (Klevins et al., (2007) Estimating health care-associated infections and deaths in U.S. hospitals. *Public Health Reports*, 122, 160-166; Scott, R. (2009) *The direct medical costs of healthcare-associated infections in U.S. hospitals and benefits of prevention* (Centers for Disease Control and Prevention, Atlanta GA)). Worldwide, the bacterial infectious disease tuberculosis kills nearly 2 million persons each year. One third of the world's population currently is infected with tuberculosis, and the World Health Organization projects that there will be nearly 1 billion new infections by 2020, 200 million of which will result in serious illness, and 35 million of which will result in death. Bacterial infectious diseases also are potential instruments of biowarfare and bioterrorism.

For six decades, antibiotics have been a bulwark against bacterial infectious diseases. This bulwark is failing due to the appearance of resistant bacterial strains. For all major bacterial pathogens, strains resistant to at least one current antibiotic have arisen. For several bacterial pathogens, including tuberculosis, strains resistant to all current antibiotics have arisen.

Bacterial RNA polymerase (RNAP) is a proven target for antibacterial therapy (Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. & Leonetti, J. (2007) *Drug Discov. Today* 12, 200-208; Ho, M., Hudson, B., Das, K., Arnold, E., Ebright, R. (2009) *Curr. Opin. Struct. Biol.* 19, 715-723; and Srivastava et al. (2011) *Curr. Opin. Microbiol.* 14, 532-543). The suitability of bacterial RNAP as a target for antibacterial therapy follows from the fact that bacterial RNAP is an essential enzyme (permitting efficacy), the fact that bacterial RNAP subunit sequences are highly conserved (permitting broad-spectrum activity), and the fact that bacterial RNAP-subunit sequences are highly conserved in human RNAP I, RNAP II, and RNAP III (permitting therapeutic selectivity).

The rifamycin antibacterial agents function by binding to and inhibiting bacterial RNAP (Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. & Leonetti, J. (2007) *Drug Discov. Today* 12, 200-208; and Ho, M., Hudson, B., Das, K., Arnold, E., Ebright, R. (2009) *Curr. Opin. Struct. Biol.* 19, 715-723). The rifamycins bind to a site on bacterial RNAP adjacent to the RNAP active center and prevent extension of RNA chains beyond a length of 2-3 nt. The rifamycins are in current clinical use in treatment of both Gram-positive and Gram-negative bacterial infections. The rifamycins are of particular importance in treatment of tuberculosis; the rifamycins are first-line anti-tuberculosis agents and are among the few antituberculosis agents able to kill non-replicating tuberculosis bacteria.

The clinical utility of the rifamycin antibacterial agents is threatened by the existence of bacterial strains resistant to rifamycins (Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. & Leonetti, J. (2007) *Drug Discov. Today* 12, 200-208; and Ho, M., Hudson, B., Das, K., Arnold, E., Ebright, R. (2009) *Curr. Opin. Struct. Biol.* 19, 715-723). Resistance to rifamycins typically involves substitution of residues in or immediately adjacent to the rifamycin binding site on bacterial RNAP—i.e., substitutions that directly decrease binding of rifamycins.

In view of the public-health threat posed by rifamycin-resistant and multidrug-resistant bacterial infections, there is an urgent need for new antibacterial agents that (i) inhibit bacterial RNAP (and thus have the same biochemical effects as rifamycins), but that (ii) inhibit bacterial RNAP through binding sites that do not overlap the rifamycin binding site (and thus do not share cross-resistance with rifamycins.

A new drug target—the "switch region"—within the structure of bacterial RNAP has been identified (WO2007/094799; Mukhopadhyay, J. et al. (2008) *Cell.* 135, 295-307; see also Belogurov, G. et al. (2009) *Nature.* 45, 332-335; Ho et al. (2009) *Curr. Opin. Struct. Biol.* 19, 715-723; Srivastava et al. (2011) *Curr. Opin. Microbiol.* 14, 532-543). The switch region is a structural element that mediates conformational changes required for RNAP to bind and retain the DNA template in transcription. The switch region is located at the base of the RNAP active-center cleft and serves as the hinge that mediates opening of the active-center cleft to permit DNA binding and that mediates closing of the active-center cleft to permit DNA retention. The switch region can serve as a binding site for compounds that inhibit bacterial gene expression and kill bacteria. Since the switch region is highly conserved in bacterial species, compounds that bind to the switch region are active against a broad spectrum of bacterial species. Since the switch region does not overlap the rifamycin binding site, compounds that bind to the switch region are not cross-resistant with rifamycins.

It has been shown that the α-pyrone antibiotic myxopyronin (Myx) functions through interactions with the bacterial RNAP switch region (WO2007/094799; Mukhopadhyay, J. et al. (2008) *Cell.* 135, 295-307; see also Belogurov, G. et al. (2009) *Nature.* 45, 332-335; Ho et al. (2009) *Curr. Opin. Struct. Biol.* 19, 715-723; Srivastava et al. (2011) *Curr. Opin. Microbiol.* 14, 532-543). Myx binds to the RNAP switch region, traps the RNAP switch region in a single conformational state, and interferes with formation of a catalytically competent transcription initiation complex. Amino acid substitutions within RNAP that confer resistance to Myx occur only within the RNAP switch region.

There is no overlap between amino acid substitutions that confer resistance to Myx and amino acid substitutions that confer resistance to rifamycins and, accordingly, there is no cross-resistance between Myx and rifamycins.

A crystal structure of a non-pathogenic bacterial RNAP, *Thermus thermophilus* RNAP, in complex with Myx has been determined, and homology models of pathogenic bacterial RNAP, including *Mycobacterium tuberculosis* RNAP and *Staphylococcus aureus* RNAP, in complex with Myx have been constructed (WO2007/094799; Mukhopadhyay, J. et al. (2008) *Cell.* 135, 295-307; see also Belogurov, G. et al. (2009) *Nature.* 45, 332-335; Ho et al. (2009) *Curr. Opin. Struct. Biol.* 19, 715-723; Srivastava et al. (2011) *Curr. Opin. Microbiol.* 14, 532-543). The crystal structure and homology models define interactions between RNAP and Myx and can be used to understand the roles of the "west" and "east" Myx sidechains as well as the Myx α-pyrone core.

U.S. Pat. Nos. 9,133,155, 9,187,446, 9,315,495 and 9,592,221 relate to pyronin compounds that are reported to possess antibacterial activity. There is a need for pyronin antibacterial compounds with improved solubility.

SUMMARY OF THE INVENTION

The invention provides methods of preparing salts containing 2-oxo-3,4-dihydro-2H-pyran-4-olate derivatives of pyronins, methods of formulating salts containing 3-acyl-2-oxo-3,4-dihydro-2H-pyran-4-olate derivatives of pyronins, and formulations of salts containing 3-acyl-2-oxo-3,4-dihydro-2H-pyran-4-olate derivatives of pyronins. The new methods and new formulations are anticipated to have applications in control of bacterial gene expression, control of bacterial growth, antibacterial prophylaxis, antibacterial therapy, and drug discovery.

Applicant has discovered that salts containing 2-oxo-3,4-dihydro-2H-pyran-4-olate derivatives of pyronins can be prepared readily, are stable, and are surprisingly highly soluble in co-solvent-free, surfactant-free, near-neutral-pH aqueous vehicles—more than an order of magnitude more soluble than the corresponding free acids.

Methods and formulations of this invention are suitable for single-day or multi-day intravenous dosing in mammals, including humans.

Methods and formulations of this invention are suitable for single-day or multi-day oral dosing in mammals, including humans.

An object of the invention is to provide antibacterial salts that possess improved aqueous solubility. Improved aqueous solubility allows for one or more of the following: formulation in co-solvent-free, surfactant-free aqueous vehicles, preparation of formulations suitable for single-day or multi-day intravenous administration at effective doses, and preparation of formulations suitable for single-day or multi-day oral administration at effective doses. Applicant has discovered that the salts of formulae Ia, Ib, Ic, and Id described herein exhibit markedly improved aqueous solubility.

The salts of the invention have utility as inhibitors of bacterial RNAP.

The salts of the invention also have utility as inhibitors of bacterial growth.

A particular object of this invention is to provide salts and pharmaceutical compositions that have utility in the treatment of bacterial infection in a mammal.

Accordingly, in one embodiment the invention provides a salt of formula Ia, Ib, Ic, or Id:

Ia

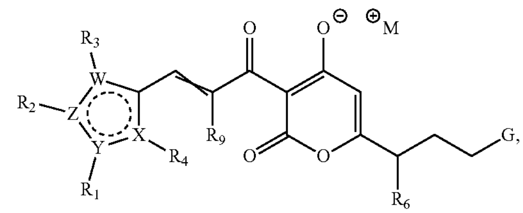

Ib

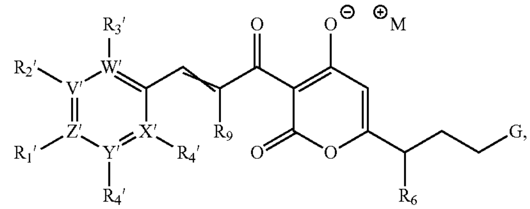

Ic

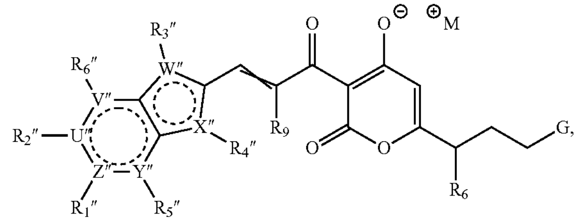

Id 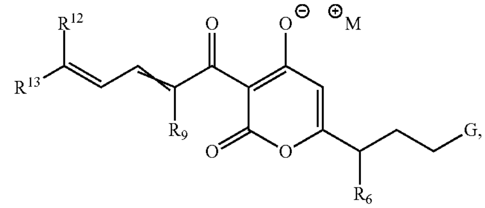 wherein:

W is sulfur, oxygen, or nitrogen;

X, Y, and Z are individually carbon, sulfur, oxygen, or nitrogen, wherein at least two of X, Y, and Z are carbon;

one of $R^1$ and $R^2$ is $C_1$-$C_{10}$ alkyl, $C_2$-$C_{10}$ alkenyl, alkoxy, aryloxy, heteroaryloxy, or $NR^aR^b$, wherein any $C_1$-$C_{10}$ alkyl, $C_2$-$C_{10}$ alkenyl, or $C_1$-$C_{10}$ alkoxy, is optionally substituted by at least one of halogen, hydroxy, $C_1$-$C_5$ alkoxy, tetrahydrofuranyl, or furanyl, and wherein any aryloxy or heteroaryloxy is optionally substituted by at least one of halogen, hydroxy, $C_1$-$C_5$ alkyl, $C_1$-$C_5$ alkoxy, aryl, or heteroaryl, wherein any $C_1$-$C_5$ alkyl, $C_1$-$C_5$ alkoxy, aryl, and heteroaryl is optionally substituted by at least one of halogen, hydroxy, $C_1$-$C_5$ alkyl, or $C_1$-$C_5$ alkoxy; or one of $R^1$ and $R^2$ is a 5-6-membered saturated, partially unsaturated, or aromatic heterocycle that is optionally substituted by at least one of halogen, hydroxy, $C_1$-$C_{10}$ alkyl, $C_2$-$C_{10}$ alkenyl, or $C_1$-$C_{10}$ alkoxy; and the other of $R^1$ and $R^2$ is absent or is one of H, halogen, $C_1$-$C_{10}$ alkyl, $C_2$-$C_{10}$ alkenyl, or $C_1$-$C_{10}$ alkoxy, wherein any $C_1$-$C_{10}$ alkyl, $C_2$-$C_{10}$ alkenyl, or $C_1$-$C_{10}$ alkoxy is optionally substituted by at least one of halogen, hydroxy, or $C_1$-$C_5$ alkoxy;

$R^3$ is absent, or is one of H, $C_1$-$C_2$ alkyl, or halogen-substituted $C_1$-$C_2$ alkyl;

R$^4$ is absent, or is one of H, halogen, C$_1$-C$_2$ alkyl, or halogen-substituted C$_1$-C$_2$ alkyl;

V', W', X', Y', and Z' are individually carbon or nitrogen; wherein at least three of V', W', X', Y', and Z' are carbon;

one of R$^{1'}$ and R$^{2'}$ is C$_1$-C$_{10}$ alkyl, C$_2$-C$_{10}$ alkenyl, C$_1$-C$_{10}$ alkoxy, aryloxy, heteroaryloxy, or NR$^a$R$^b$, wherein any C$_1$-C$_{10}$ alkyl, C$_2$-C$_{10}$ alkenyl, or C$_1$-C$_{10}$ alkoxy, is optionally substituted by at least one of halogen, hydroxy, C$_1$-C$_5$ alkoxy, tetrahydrofuranyl, or furanyl, and wherein any aryloxy or heteroaryloxy is optionally substituted by at least one of halogen, hydroxy, C$_1$-C$_5$ alkyl, C$_1$-C$_5$ alkoxy, aryl, or heteroaryl, wherein any C$_1$-C$_5$ alkyl, C$_1$-C$_5$ alkoxy, aryl, and heteroaryl is optionally substituted by at least one of halogen, hydroxy, C$_1$-C$_5$ alkyl, or C$_1$-C$_5$ alkoxy;

or one of R$^{1'}$ and R$^{2'}$ is a 5-6-membered saturated, partially unsaturated, or aromatic heterocycle that is optionally substituted by at least one of halogen, hydroxy, C$_1$-C$_{10}$ alkyl, C$_2$-C$_{10}$ alkenyl, or C$_1$-C$_{10}$ alkoxy; and the other of R$^{1'}$ and R$^{2'}$ is absent or is one of H, halogen, C$_1$-C$_{10}$ alkyl, C$_2$-C$_{10}$ alkenyl, or C$_1$-C$_{10}$ alkoxy, wherein any C$_1$-C$_{10}$ alkyl, C$_2$-C$_{10}$ alkenyl, or C$_1$-C$_{10}$ alkoxy is optionally substituted by at least one of halogen, hydroxy, or C$_1$-C$_5$ alkoxy; R$^{3'}$, R$^{4'}$, and R$^{5'}$ are each independently absent, H, halogen, C$_1$-C$_2$ alkyl, or halogen-substituted C$_1$-C$_2$ alkyl;

W" is sulfur, oxygen, or nitrogen;

U", V", X", Y", and Z" are individually carbon, sulfur, oxygen, or nitrogen, wherein at least three of U", V", X", Y", and Z" are carbon;

one of R$^{1''}$ and R$^{2''}$ is C$_1$-C$_{10}$ alkyl, C$_2$-C$_{10}$ alkenyl, C$_1$-C$_{10}$ alkoxy, aryloxy, heteroaryloxy, or NR$^a$R$^b$, wherein any C$_1$-C$_{10}$ alkyl, C$_2$-C$_{10}$ alkenyl, or C$_1$-C$_{10}$ alkoxy, is optionally substituted by at least one of halogen, hydroxy, C$_1$-C$_5$ alkoxy, tetrahydrofuranyl, or furanyl, and wherein any aryloxy or heteroaryloxy is optionally substituted by at least one of halogen, hydroxy, C$_1$-C$_5$ alkyl, C$_1$-C$_5$ alkoxy, aryl, or heteroaryl, wherein any C$_1$-C$_5$ alkyl, C$_1$-C$_5$ alkoxy, aryl, and heteroaryl is optionally substituted by at least one of halogen, hydroxy, C$_1$-C$_5$ alkyl, or C$_1$-C$_5$ alkoxy; or one of R$^{1''}$ and R$^{2''}$ is a 5-6-membered saturated, partially unsaturated, or aromatic heterocycle that is optionally substituted by at least one of halogen, hydroxy, C$_1$-C$_{10}$ alkyl, C$_2$-C$_{10}$ alkenyl, or C$_1$-C$_{10}$ alkoxy; and the other of R$^{1''}$ and R$^{2''}$ is absent or is one of H, halogen, C$_1$-C$_{10}$ alkyl, C$_2$-C$_{10}$ alkenyl, or C$_1$-C$_{10}$ alkoxy, wherein any C$_1$-C$_{10}$ alkyl, C$_2$-C$_{10}$ alkenyl, or C$_1$-C$_{10}$ alkoxy is optionally substituted by at least one of halogen, hydroxy, or C$_1$-C$_5$ alkoxy;

R$^{3''}$ is absent or is one of H, C$_1$-C$_2$ alkyl, or halogen-substituted C$_1$-C$_2$ alkyl;

R$^{4''}$, R$^{5''}$, and R$^{6''}$ are each independently absent, H, halogen, C$_1$-C$_2$ alkyl, or halogen-substituted C$_1$-C$_2$ alkyl;

R$^6$ is H, halogen, or methyl that is optionally substituted by halogen;

G is one of —CH=CH—NHC(O)—R$^7$, —CH=CH—NHC(S)—R$^7$, —CH$_2$CH$_2$NHC(O)—R$^7$, —CH$_2$CH$_2$NHC(S)—R$^7$, —CH$_2$NHNHC(O)—R$^7$, or —CH$_2$NHNHC(S)—R$^7$, R$^7$ is one of C$_1$-C$_6$ alkyl, —O(C$_1$-C$_6$ alkyl), —S(C$_1$-C$_6$ alkyl), or —N(R$^8$)$_2$;

each R$^8$ is independently one of hydrogen or —C$_1$-C$_6$ alkyl;

R$^9$ is C$_1$-C$_{10}$ alkyl or C$_2$-C$_{10}$ alkenyl, wherein any C$_1$-C$_{10}$ alkyl or C$_2$-C$_{10}$ alkenyl is optionally substituted by at least one of halogen, hydroxy, alkoxy, or NR$^a$R$^b$;

one of R$^{12}$ and R$^{13}$ is hydrogen or C$_1$-C$_4$ straight alkyl, and the other of R$^{12}$ and R$^{13}$ is C$_1$-C$_{10}$ straight or branched alkyl, C$_2$-C$_{12}$ straight or branched hydroxyalkyl, C$_2$-C$_{12}$ straight or branched alkenyl, C$_2$-C$_{12}$ straight or branched hydroxyalkenyl, phenyl, C$_7$-C$_{12}$ aralkyl, C$_7$-C$_{12}$ (aryl)hydroxyalkyl, C$_6$-C$_{12}$ heteroaralkyl, C$_6$-C$_{12}$ (heteroaryl)hydroxyalkyl, or R$^{12}$ and R$^{13}$ are taken together with their intervening atom to form a 4-6 membered ring having 0-1 ring heteroatoms selected from nitrogen, oxygen or sulfur, said ring optionally substituted by one or two C$_1$-C$_6$ alkyl, C$_2$-C$_6$ alkenyl or hydroxyalkyl groups, wherein an alkyl, aryl or heteroaryl moiety of R$^{12}$ and R$^{13}$ optionally is substituted with 1-3 groups independently selected from halo, —C$_1$-C$_6$ hydroxyalkyl, —C$_1$-C$_4$ alkoxy, —C$_1$-C$_4$ trifluoroalkoxy, —CN, —C$_1$-C$_4$ alkoxycarbonyl, —C$_1$-C$_4$ alkylcarbonyl, —S(C$_1$-C$_4$ alkyl), and —SO$_2$(C$_1$-C$_4$ alkyl);

each R$^a$ is independently C$_1$-C$_{10}$ alkyl that is optionally substituted by at least one of halogen, hydroxy, or C$_1$-C$_5$ alkoxy;

each R$^b$ is independently H or C$_1$-C$_{10}$ alkyl that is optionally substituted by at least one of halogen, hydroxy, or C$_1$-C$_5$ alkoxy; and M$^+$ is a pharmaceutically acceptable cation. The invention also provides a salt of formula Ia, Ib, Ic, or Id for use in medical treatment.

The invention also provides a salt of formula Ia, Ib, Ic, or Id for use in the prophylaxis or treatment of a bacterial infection.

The invention also provides a composition comprising a salt of formula Ia, Ib, Ic, or Id and a pharmaceutically acceptable carrier. In one embodiment the composition is sutable for intravenous administration. In one embodiment the pharmaceutically acceptable carrier is water. In one embodiment the composition is substantially free of organic co-solvents. In one embodiment the composition is substantially free of surfactants. The invention also provides the use of a salt of the invention as an inhibitor of a bacterial RNA polymerase.

The invention also provides the use of a salt of the invention as an antibacterial agent.

The invention also provides the use of a salt of the invention as a disinfectant, a sterilant, an antispoilant, an antiseptic, or an antiinfective.

The invention also provides the use of a salt of formula Ia, Ib, Ic, or Id for the preparation of a medicament for prophylaxis or treatment of a bacterial infection in a mammal.

The invention also provides a method of inhibiting a bacterial RNA polymerase, comprising contacting a bacterial RNA polymerase with a salt of the invention.

The invention also provides a method of treating a bacterial infection in a mammal, comprising administering to the mammal a therapeutically effective amount of a salt of formula Ia, Ib, Ic, or Id.

DETAILED DESCRIPTION OF THE INVENTION

Definitions

The following definitions are used, unless otherwise indicated.

The term "halo" means fluoro, chloro, bromo, or iodo.

The term "alkyl" used alone or as part of a larger moiety, includes both straight and branched chains. For example, $C_1-C_{10}$ alkyl includes both straight and branched chained alkyl groups having from one to ten carbon atoms. The term alkyl also includes cycloalkyl groups (e.g. cyclopropyl, cyclobutyl, cyclopently, cyclohexyl, cycloheptyl, and cyclooctyl), as well as (cycloalkyl)alkyl groups (e.g. 3-cyclohexylpropyl, cyclopentylmethyl, 2-cyclohexylethyl, and 2-cyclopropylethyl).

The term "alkenyl" used alone or as part of a larger moiety, includes an alkyl that has one or more double bonds. For example, $C_2-C_{10}$ alkenyl includes both straight and branched chained groups having from two to ten carbon atoms and one or more (e.g. 1, 2, or 3) double bonds, as well as (cycloalkyl)alkyl groups having one or more double bonds in the cycloalkyl portion or in the alkyl portion of the (cycloalkyl)alkyl.

The term "alkoxy" used alone or as part of a larger moiety is a group alkyl-O—, wherein alkyl has any of the values defined herein.

The term "aryl" denotes a phenyl radical or an ortho-fused bicyclic carbocyclic radical having about nine to ten ring atoms in which at least one ring is aromatic. For example, aryl can be phenyl, indenyl, or naphthyl.

The term "heteroaryl" encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$ alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X). For example heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

The term "heterocycle" or "heterocyclyl" ring as used herein refers to a ring that has at least one atom other than carbon in the ring, wherein the atom is selected from the group consisting of oxygen, nitrogen and sulfur. The ring can be saturated, partially unsaturated, or aromatic. The term includes single (e.g., monocyclic) saturated, partially unsaturated, and aromatic rings (e.g., 3, 4, 5, 6 or 7-membered rings) from about 1 to 6 carbon atoms and from about 1 to 4 heteroatoms selected from the group consisting of oxygen, nitrogen and sulfur in the ring. In one embodiment the term includes 5-6 membered saturated, partially unsaturated, and aromatic heterocycles that include 1-5 carbon atoms and 1-4 heteroatoms.

A bond designated ⇌ herein represents a double bond that can optionally be cis, trans, or a mixture thereof.

A combination of substituents or variables is permissible only if such a combination results in a stable or chemically feasible salt. The term "stable salts," as used herein, refers to salts which possess stability sufficient to allow for their manufacture and which maintain the integrity of the salt for a sufficient period of time to be useful for the purposes detailed herein (e.g., formulation into therapeutic products, intermediates for use in production of therapeutic salts, isolatable or storable intermediate salts, treating a disease or condition responsive to therapeutic agents.

Unless otherwise stated, structures depicted herein are also meant to include all stereochemical forms of the structure (i.e., the R and S configurations for each asymmetric center). Therefore, single stereochemical isomers, as well as enantiomeric and diastereomeric mixtures, of the present salts are within the scope of the invention. Similarly, E- and Z-isomers, or mixtures thereof, of olefins within the structures also are within the scope of the invention.

Unless otherwise stated, structures depicted herein also are meant to include salts that include one or more isotopically enriched atoms. For example, salts having the present structures except for the replacement of a hydrogen atom by a deuterium or tritium, or the replacement of a carbon by a $^{13}C$- or $^{14}C$-enriched carbon, are within the scope of this invention.

Salts of this invention may exist in tautomeric forms, such as keto-enol tautomers. The depiction of a single tautomer is understood to represent the salt in all of its tautomeric forms.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio.

The term "pharmaceutically acceptable cation" includes sodium, potassium, lithium, ammonium, calcium, magnesium, iron, zinc, copper, manganese, aluminum and the like. Particularly acceptable cations are the monovalent catins, including sodium, potassium, lithium, and ammonium, and the like. The term pharmaceutically acceptable cation" also includes cations formed by protonation or alkylation of a pharmaceutically acceptable organic nontoxic bases such as primary, secondary, and tertiary amines, substituted amines including naturally occurring substituted amines, cyclic amines and basic ion exchange resins. For example, the term "pharmaceutically acceptable cation" includes cations formed from unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—$(C_1-C_6)$-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

Antibacterial Agents

The invention provides new compositions of matter that highly potently inhibit bacterial RNA polymerase and inhibit bacterial growth. Certain embodiments of the invention also provide methods for preparation of a salt according to general structural formula (Ia), (Ib), (Ic), or (Id).

Certain embodiments of the invention also provide an assay for inhibition of a RNA polymerase comprising contacting a bacterial RNA polymerase with a salt according to general structural formula (Ia), (Ib), (Ic), or (Id).

Certain embodiments of the invention also provide an assay for antibacterial activity comprising contacting a bacterial RNA polymerase with a salt according to general structural formula (Ia), (Ib), (Ic), or (Id).

Certain embodiments of the invention also provide the use of a salt according to general structural formula (Ia), (Ib), (Ic), or (Id) as an inhibitor of a bacterial RNA polymerase.

Certain embodiments of the invention also provide the use of a salt according to general structural formula (Ia), (Ib), (Ic), or (Id) as an antibacterial agent.

Certain embodiments of the invention also provide the use of a salt according to general structural formula (Ia), (Ib), (Ic), or (Id) as one of a disinfectant, a sterilant, an antispoilant, an antiseptic, or an antiinfective.

In a certain embodiment for a salt of formula Ia, Ib, Ic, or Id:

W is sulfur, oxygen, or nitrogen;

X, Y, and Z are individually carbon, sulfur, oxygen, or nitrogen, wherein at least two of X, Y, and Z are carbon;

one of $R^1$ and $R^2$ is $C_1$-$C_{10}$ alkyl, $C_2$-$C_{10}$ alkenyl, $C_1$-$C_{10}$ alkoxy, aryloxy, heteroaryloxy, or $NR^aR^b$, wherein any $C_1$-$C_{10}$ alkyl, $C_2$-$C_{10}$ alkenyl, or $C_1$-$C_{10}$ alkoxy, is optionally substituted by at least one of halogen, hydroxy, $C_1$-$C_5$ alkoxy, tetrahydrofuranyl, or furanyl, and wherein any aryloxy or heteroaryloxy is optionally substituted by at least one of halogen, hydroxy, $C_1$-$C_5$ alkyl, or $C_1$-$C_5$ alkoxy, wherein any $C_1$-$C_5$ alkyl and $C_1$-$C_5$ alkoxy is optionally substituted by at least one of halogen, hydroxy, or $C_1$-$C_5$ alkoxy; or one of $R^1$ and $R^2$ is a 5-6-membered saturated, partially unsaturated, or aromatic heterocycle that is optionally substituted by at least one of halogen, hydroxy, $C_1$-$C_{10}$ alkyl, $C_2$-$C_{10}$ alkenyl, or $C_1$-$C_{10}$ alkoxy; and the other of $R^1$ and $R^2$ is absent or is one of H, halogen, $C_1$-$C_{10}$ alkyl, $C_2$-$C_{10}$ alkenyl, or $C_1$-$C_{10}$ alkoxy, wherein any $C_1$-$C_{10}$ alkyl, $C_2$-$C_{10}$ alkenyl, or $C_1$-$C_{10}$ alkoxy is optionally substituted by at least one of halogen, hydroxy, or $C_1$-$C_5$ alkoxy;

$R^3$ is absent, or is one of H, $C_1$-$C_2$ alkyl, or halogen-substituted $C_1$-$C_2$ alkyl;

$R^4$ is absent, or is one of H, halogen, $C_1$-$C_2$ alkyl, or halogen-substituted $C_1$-$C_2$ alkyl;

V', W', X', Y', and Z' are individually carbon or nitrogen; wherein at least three of V', W', X', Y', and Z' are carbon;

one of $R^{1'}$ and $R^{2'}$ is $C_1$-$C_{10}$ alkyl, $C_2$-$C_{10}$ alkenyl, $C_1$-$C_{10}$ alkoxy, aryloxy, heteroaryloxy, or $NR^aR^b$, wherein any $C_1$-$C_{10}$ alkyl, $C_2$-$C_{10}$ alkenyl, or $C_1$-$C_{10}$ alkoxy, is optionally substituted by at least one of halogen, hydroxy, $C_1$-$C_5$ alkoxy, tetrahydrofuranyl, or furanyl, and wherein any aryloxy or heteroaryloxy is optionally substituted by at least one of halogen, hydroxy, $C_1$-$C_5$ alkyl, or $C_1$-$C_5$ alkoxy, wherein any $C_1$-$C_5$ alkyl and $C_1$-$C_5$ alkoxy is optionally substituted by at least one of halogen, hydroxy, or $C_1$-$C_5$ alkoxy; or one of $R^{1'}$ and $R^{2'}$ is a 5-6-membered saturated, partially unsaturated, or aromatic heterocycle that is optionally substituted by at least one of halogen, hydroxy, $C_1$-$C_{10}$ alkyl, $C_2$-$C_{10}$ alkenyl, or $C_1$-$C_{10}$ alkoxy; and the other of $R^{1'}$ and $R^{2'}$ is absent or is one of H, halogen, $C_1$-$C_{10}$ alkyl, $C_2$-$C_{10}$ alkenyl, or $C_1$-$C_{10}$ alkoxy, wherein any $C_1$-$C_{10}$ alkyl, $C_2$-$C_{10}$ alkenyl, or $C_1$-$C_{10}$ alkoxy is optionally substituted by at least one of halogen, hydroxy, or $C_1$-$C_5$ alkoxy;

$R^{3'}$, $R^{4'}$, and $R^{5'}$ are each independently absent, H, halogen, $C_1$-$C_2$ alkyl, or halogen-substituted $C_1$-$C_2$ alkyl;

W" is sulfur, oxygen, or nitrogen;

U", V", X", Y", and Z" are individually carbon, sulfur, oxygen, or nitrogen, wherein at least three of U", V", X", Y", and Z" are carbon;

one of $R^{1''}$ and $R^{2''}$ is $C_1$-$C_{10}$ alkyl, $C_2$-$C_{10}$ alkenyl, $C_1$-$C_{10}$ alkoxy, aryloxy, heteroaryloxy, or $NR^aR^b$, wherein any $C_1$-$C_{10}$ alkyl, $C_2$-$C_{10}$ alkenyl, or $C_1$-$C_{10}$ alkoxy, is optionally substituted by at least one of halogen, hydroxy, $C_1$-$C_5$ alkoxy, tetrahydrofuranyl, or furanyl, and wherein any aryloxy or heteroaryloxy is optionally substituted by at least one of halogen, hydroxy, $C_1$-$C_5$ alkyl, or $C_1$-$C_5$ alkoxy, wherein any $C_1$-$C_5$ alkyl and $C_1$-$C_5$ alkoxy is optionally substituted by at least one of halogen, hydroxy, or $C_1$-$C_5$ alkoxy; or one of $R^{1''}$ and $R^{2''}$ is a 5-6-membered saturated, partially unsaturated, or aromatic heterocycle that is optionally substituted by at least one of halogen, hydroxy, $C_1$-$C_{10}$ alkyl, $C_2$-$C_{10}$ alkenyl, or $C_1$-$C_{10}$ alkoxy; and the other of $R^{1''}$ and $R^{2''}$ is absent or is one of H, halogen, $C_1$-$C_{10}$ alkyl, $C_2$-$C_{10}$ alkenyl, or $C_1$-$C_{10}$ alkoxy, wherein any $C_1$-$C_{10}$ alkyl, $C_2$-$C_{10}$ alkenyl, or $C_1$-$C_{10}$ alkoxy is optionally substituted by at least one of halogen, hydroxy, or $C_1$-$C_5$ alkoxy;

$R^{3''}$ is absent or is one of H, $C_1$-$C_2$ alkyl, or halogen-substituted $C_1$-$C_2$ alkyl;

$R^{4''}$, $R^{5''}$, and $R^{6''}$ are each independently absent, H, halogen, $C_1$-$C_2$ alkyl, or halogen-substituted $C_1$-$C_2$ alkyl;

$R^6$ is H, halogen, or methyl that is optionally substituted by halogen;

G is one of —CH=CH—NHC(O)—$R^7$, —CH=CH—NHC(S)—$R^7$, —CH$_2$CH$_2$NHC(O)—$R^7$, —CH$_2$CH$_2$NHC(S)—$R^7$, —CH$_2$NHNHC(O)—$R^7$, or —CH$_2$NHNHC(S)—$R^7$, $R^7$ is one of $C_1$-$C_6$ alkyl, —O($C_1$-$C_6$ alkyl), —S($C_1$-$C_6$ alkyl), or —N($R^8$)$_2$;

each $R^8$ is independently one of hydrogen or —$C_1$-$C_6$ alkyl;

$R^9$ is $C_1$-$C_{10}$ alkyl or $C_2$-$C_{10}$ alkenyl, wherein any $C_1$-$C_{10}$ alkyl or $C_2$-$C_{10}$ alkenyl is optionally substituted by at least one of halogen, hydroxy, alkoxy, or $NR^aR^b$;

one of $R^{12}$ and $R^{13}$ is hydrogen or $C_1$-$C_4$ straight alkyl, and the other of $R^{12}$ and $R^{13}$ is $C_1$-$C_{10}$ straight or branched alkyl, $C_2$-$C_{12}$ straight or branched hydroxyalkyl, $C_2$-$C_{12}$ straight or branched alkenyl, $C_2$-$C_{12}$ straight or branched hydroxyalkenyl, phenyl, $C_7$-$C_{12}$ aralkyl, $C_7$-$C_{12}$ (aryl)hydroxyalkyl, $C_6$-$C_{12}$ heteroaralkyl, $C_6$-$C_{12}$ (heteroaryl)hydroxyalkyl, or $R^{12}$ and $R^{13}$ are taken together with their intervening atom to form a 4-6 membered ring having 0-1 ring heteroatoms selected from nitrogen, oxygen or sulfur, said ring optionally substituted by one or two $C_1$-$C_6$ alkyl, $C_2$-$C_6$ alkenyl or hydroxyalkyl groups, wherein an alkyl, aryl or heteroaryl moiety of $R^{12}$ and $R^{13}$ optionally is substituted with 1-3 groups independently selected from halo, —$C_1$-$C_6$ hydroxyalkyl, —$C_1$-$C_4$ alkoxy, —$C_1$-$C_4$ trifluoroalkoxy, —CN, —$C_1$-$C_4$ alkoxycarbonyl, —$C_1$-$C_4$ alkylcarbonyl, —S($C_1$-$C_4$ alkyl), and —SO$_2$($C_1$-$C_4$ alkyl);

each $R^a$ is independently $C_1$-$C_{10}$ alkyl that is optionally substituted by at least one of halogen, hydroxy, or $C_1$-$C_5$ alkoxy;

each $R^b$ is independently H or $C_1$-$C_{10}$ alkyl that is optionally substituted by at least one of halogen, hydroxy, or $C_1$-$C_5$ alkoxy; and $M^+$ is a pharmaceutically acceptable cation.

In a certain embodiment the salt of formula Ia is a salt of Ia' and the salt of formula Id is a salt of formula Id'

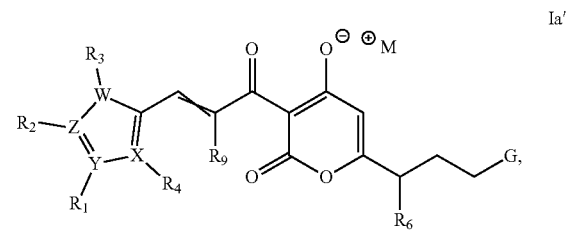

Ia'

-continued

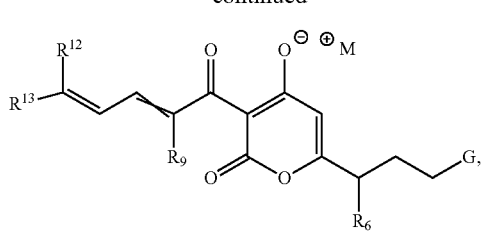

wherein:
W is sulfur, oxygen, or nitrogen;
X, Y, and Z are individually carbon, or nitrogen, wherein at least two of X, Y, and Z are carbon;
one of $R^1$ and $R^2$ is $C_1$-$C_{10}$ alkyl, $C_2$-$C_{10}$ alkenyl, $C_1$-$C_{10}$ alkoxy, aryloxy, heteroaryloxy, or $NR^aR^b$, wherein any $C_1$-$C_{10}$ alkyl, $C_2$-$C_{10}$ alkenyl, or $C_1$-$C_{10}$ alkoxy, is optionally substituted by at least one of halogen, hydroxy, $C_1$-$C_5$ alkoxy, tetrahydrofuranyl, or furanyl, and wherein any aryloxy or heteroaryloxy is optionally substituted by at least one of halogen, hydroxy, $C_1$-$C_5$ alkyl, $C_1$-$C_5$ alkoxy, aryl, or heteroaryl, wherein any $C_1$-$C_5$ alkyl, $C_1$-$C_5$ alkoxy, aryl, and heteroaryl is optionally substituted by at least one of halogen, hydroxy, $C_1$-$C_5$ alkyl, or $C_1$-$C_5$ alkoxy; or one of $R^1$ and $R^2$ is a 5-6-membered saturated, partially unsaturated, or aromatic heterocycle that is optionally substituted by at least one of halogen, hydroxy, $C_1$-$C_{10}$ alkyl, $C_2$-$C_{10}$ alkenyl, or $C_1$-$C_{10}$ alkoxy; and the other of $R^1$ and $R^2$ is absent or is one of H, halogen, $C_1$-$C_{10}$ alkyl, $C_2$-$C_{10}$ alkenyl, or $C_1$-$C_{10}$ alkoxy, wherein any $C_1$-$C_{10}$ alkyl, $C_2$-$C_{10}$ alkenyl, or $C_1$-$C_{10}$ alkoxy is optionally substituted by at least one of halogen, hydroxy, or $C_1$-$C_5$ alkoxy;
$R^3$ is absent, or is one of H, $C_1$-$C_2$ alkyl, or halogen-substituted $C_1$-$C_2$ alkyl;
$R^4$ is absent, or is one of H, halogen, $C_1$-$C_2$ alkyl, or halogen-substituted $C_1$-$C_2$ alkyl;
$R^6$ is H, halogen, or methyl that is optionally is substituted by halogen;
G is one of —CH=CH—NHC(O)—$R^7$, —CH=CH—NHC(S)—$R^7$, —CH$_2$CH$_2$NHC(O)—$R^7$, —CH$_2$CH$_2$NHC(S)—$R^7$, —CH$_2$NHNHC(O)—$R^7$, or —CH$_2$NHNHC(S)—$R^7$, $R^7$ is one of $C_1$-$C_6$ alkyl, —O($C_1$-$C_6$ alkyl), —S($C_1$-$C_6$ alkyl), or —N($R^8$)$_2$;
each $R^8$ is independently one of hydrogen or —$C_1$-$C_6$ alkyl;
$R^9$ is $C_1$-$C_{10}$ alkyl or $C_2$-$C_{10}$ alkenyl, wherein any $C_1$-$C_{10}$ alkyl or $C_2$-$C_{10}$ alkenyl is optionally substituted by at least one of halogen, hydroxy, alkoxy, or $NR^aR^b$;
one of $R^{12}$ and $R^{13}$ is hydrogen or $C_1$-$C_4$ straight alkyl, and the other of $R^{12}$ and $R^{13}$ is $C_1$-$C_{10}$ straight or branched alkyl, $C_2$-$C_{12}$ straight or branched hydroxyalkyl, $C_2$-$C_{12}$ straight or branched alkenyl, $C_2$-$C_{12}$ straight or branched hydroxyalkenyl, phenyl, $C_7$-$C_{12}$ aralkyl, $C_7$-$C_{12}$ (aryl)hydroxyalkyl, $C_6$-$C_{12}$ heteroaralkyl, $C_6$-$C_{12}$ (heteroaryl)hydroxyalkyl, or $R^{12}$ and $R^{13}$ are taken together with their intervening atom to form a 4-6 membered ring having 0-1 ring heteroatoms selected from nitrogen, oxygen or sulfur, said ring optionally substituted by one or two $C_1$-$C_6$ alkyl, $C_2$-$C_6$ alkenyl or hydroxyalkyl groups, wherein an alkyl, aryl or heteroaryl moiety of $R^{12}$ and $R^{13}$ optionally is substituted with 1-3 groups independently selected from halo, —$C_1$-$C_6$ hydroxyalkyl, —$C_1$-$C_4$ alkoxy, —$C_1$-$C_4$ trifluoroalkoxy, —CN, —$C_1$-$C_4$ alkoxycarbonyl, —$C_1$-$C_4$ alkylcarbonyl, —S($C_1$-$C_4$ alkyl), and —SO$_2$($C_1$-$C_4$ alkyl);
each $R^a$ is $C_1$-$C_{10}$ alkyl that is optionally substituted by at least one of halogen, hydroxy, or $C_1$-$C_5$ alkoxy; and
each $R^b$ is H or $C_1$-$C_{10}$ alkyl that is optionally substituted by at least one of halogen, hydroxy, or $C_1$-$C_5$ alkoxy.

In a certain embodiment the invention provides a salt of formula Ia.
In a certain embodiment the invention provides a salt of formula Ib.
In a certain embodiment the invention provides a salt of formula Ic.
In a certain embodiment the invention provides a salt of formula Id.
In a certain embodiment, $R^6$ is H.
In a certain embodiment, $R^6$ is methyl.
In a certain embodiment, $R^6$ is methyl and the salt, or a salt thereof, is a mixture of the R and S stereoisomers.
In a certain embodiment, $R^6$ is methyl and the salt, or a salt thereof, is predominantly the R stereoisomer, preferably at least 90% of the R isomer.
In a certain embodiment the invention provides a salt selected from

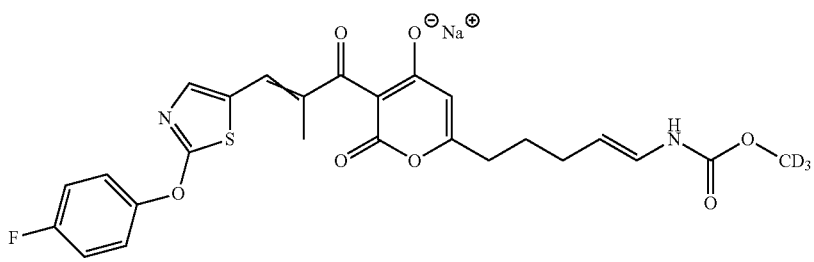

-continued

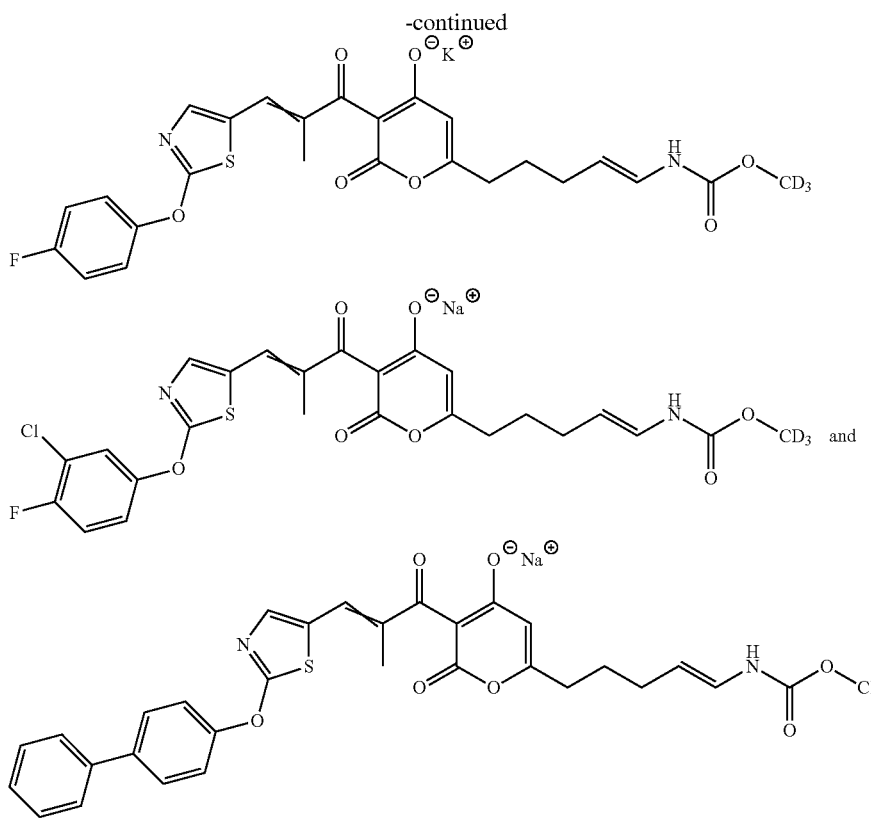

In a certain embodiment the invention provides a composition that is suitable for intravenous administration.

In a certain embodiment the invention provides a composition that comprises water as a pharmaceutically acceptable.

In a certain embodiment of the invention, the composition is substantially free of organic co-solvents.

In a certain embodiment of the invention, the composition is substantially free of surfactants.

In a certain embodiment, the invention provides a composition comprising the salt of formula (I) and water, wherein the composition is substantially co-solvent free, substantially surfactant free, and has a pH of from about 7 to about 9, and wherein the concentration of the salt is at least about 0.25 mg/mL.

In a certain embodiment, $R^7$ is not deuterated alkyl.

Salt Synthesis

Free acids of compounds corresponding to the salts of Formulae Ia-Id can be prepared, by way of example, as described in U.S. Pat. Nos. 9,133,155, 9,187,446, 9,315,495 and 9,592,221, and as in the Examples.

Starting from said free acids, the salts of Formulae Ia-Id can be prepared, by way of example, by contacting with an aqueous solution at a pH of at least about 9-10, and preferably at least about 11-12, until solids are dissolved, followed by reversed-phase solid-phase extraction or reversed-phase chromatography, for example, as shown in the Examples.

Administration of Pharmaceutical Compositions

The salts of Formulae Ia-Id may be formulated as pharmaceutical compositions and administered to a mammalian host, such as a human patient in a variety of forms adapted to the chosen route of administration (i.e., orally or parenterally, by intravenous, intramuscular, topical or subcutaneous routes).

Thus, the present salts may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active salt may be combined with one or more excipients and used in the form of ingestible tablets, buccal tablets, troches, capsules, elixirs, suspensions, syrups, wafers, and the like. Such compositions and preparations should contain at least 0.1% of active salt. The percentage of the compositions and preparations may, of course, be varied and may conveniently be between about 2 to about 60% of the weight of a given unit dosage form. The amount of active salt in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active salt, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active salt may be incorporated into sustained-release preparations and devices.

The active salt may also be administered intravenously or intraperitoneally by infusion or injection. Solutions of the active salt or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active salt in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present salts may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present salts can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the salts of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the salts of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the salt required for use in treatment will vary not only with the particular salt selected but also with the route of administration, the nature of the condition being treated and the age and condition of the patient and will be ultimately at the discretion of the attendant physician or clinician.

The salt is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a salt of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The following illustrate representative pharmaceutical dosage forms, containing a salt of formula Ia, Ib, Ic, or Id ('Salt X'), for therapeutic or prophylactic use in humans:

a) A formulation comprising from about 0.25 mg/ml to about 10 mg/ml of Salt X in about 10 mM sodium phosphate at about pH 7.4; and b) A formulation comprising from about 0.25 mg/ml to about 5 mg/ml of Salt X and about 5% dextrose in about 10 mM sodium phosphate at about pH 7.4; and c) A formulation comprising from about 0.25 mg/ml to about at least 5 mg/ml of Salt X in phosphate-buffered saline at about pH 7.4; and d) A formulation comprising from about 0.25 mg/ml to about 20 mg/ml of Salt X in about 0 to about 1% carboxymethylcellulose and about 0 to about 1% Tween 80 at about pH 8.4.

The invention will now be illustrated by the following non-limiting Examples.

EXAMPLES

Example 1: 4-hydroxy-6-(pent-4-en-1-yl)-2H-pyran-2-one

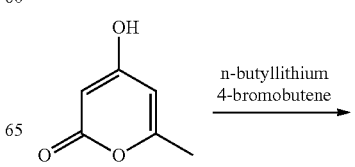

17

-continued

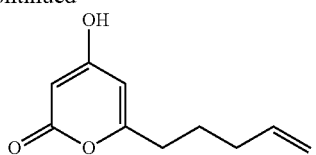

4-hydroxy-6-methyl-2H-pyran-2-one (Sigma-Aldrich; 7.57 g; 60 mmol) was dissolved in 180 ml tetrahydrofuran-hexamethylphosphoramide (Sigma-Aldrich; 150:30 v/v). The solution was cooled to −78° C.; n-butyllithium (54 mL, 2.5M, 0.135 mmol; Sigma-Aldrich) was added drop-wise over 30 min. The reaction mixture was stirred 0.5 h at −78° C., another 15 minutes at 0° C. and then brought down to −78° C. 4-Bromobutene (12.2 ml; 120 mmol; Sigma-Aldrich) was added drop-wise, and the reaction mixture was stirred overnight, allowing the temperature to increase to room temperature. The reaction was quenched with 1 M HCl to pH 2 and extracted with 4×100 ml ethyl acetate, and the ethyl acetate extracts were pooled, washed with 100 ml brine, dried over anhydrous sodium sulfate, and evaporated to an oil. The product was isolated via silica chromatography (ethyl acetate/hexanes gradient) on a CombiFlash Companion. Yield: 10.53 g (97%). $^1$H NMR (400 MHz, CDCl$_3$): δ 5.97 (s, 1H), 5.70 (m, 1H), 5.58 (s, 1H), 5.00-4.95 (m, 2H), 2.42 (t, 2H), 2.02 (m, 2H), 1.85 (m, 2H). MS (API-ESI): calculated: m/z 180.20 (MH$^+$); found: 180.91.

Example 2: 4-hydroxy-6-(pent-4-en-1-yl)-3-propionyl-2H-pyran-2-one

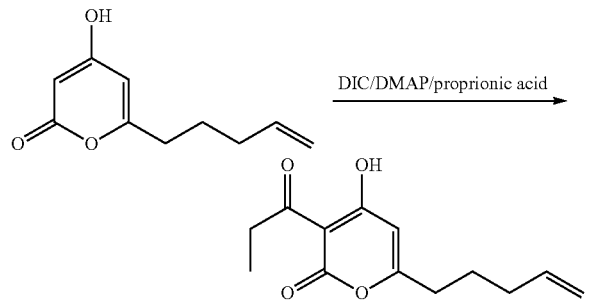

N,N'-Diisopropylcarbodiimide (Sigma-Aldrich; 0.42 ml; 2.71 mmol), 4-(dimethylamino)pyridine (Sigma-Aldrich; 30 mg; 0.25 mmol), propionic acid (Sigma-Aldrich; 0.204 mL, 2.73 mmol) and 4-hydroxy-6-(pent-4-en-1-yl)-2H-pyran-2-one (Example 1, 0.443 g, 2.46 mmol) were dissolved in 7 ml toluene and heated 4 h in a 40 mL screw cap pressure vial at 100° C. under argon. Upon cooling to 25° C., 14 ml ethyl acetate was added to the reaction mixture to precipitate the by-product DIC urea. The reaction mix was filtered, the solid was triturated with 100 mL ethyl acetate. The organic solutions were pooled and washed with 25 ml 1M HCl, 25 ml water, and 25 ml brine, and was dried over anhydrous sodium sulfate. The product was isolated via silica chromatography dichloromethane) Yield: 0.331 g (57%). $^1$HNMR (400 MHz, CDCl$_3$): δ 5.96 (s, 1H), 5.80 (m, 1H), 5.05-4.95 (m, 2H), 3.10 (q, 2H), 2.50 (t, 2H), 2.10 (m, 2H), 1.80 (m, 2H), 1.18 (t, 3H).

18

Example 3: methyl (E)-6-(4-hydroxy-2-oxo-3-propionyl-2H-pyran-6-yl)hex-2-enoate

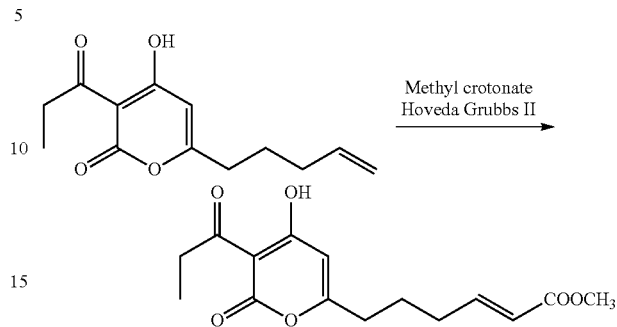

To 4-hydroxy-6-(pent-4-en-1-yl)-3-propionyl-2H-pyran-2-one (Example 2; 1.5 g; 6.3 mmol) and methyl crotonate (Sigma-Aldrich; 4.41 ml, 41.6 mmol) in 8 ml anhydrous t-butyl methyl ether, was added Hoveyda-Grubbs Catalyst II (Sigma-Aldrich; 130 mg, 0.21 mmol), and the reaction mixture was heated 16 h at 50° C. The solvent was evaporated, and the product was isolated via silica chromatography (ethyl acetate/hexanes gradient) on a CombiFlash Companion. Yield: 1.3 g (70%). $^1$H NMR (400 MHz, CDCl$_3$): δ 6.90 (m, 1H), 5.90 (s, 1H), 5.82 (d, 2H), 3.70 (s, 3H), 3.10 (q, 2H), 2.50 (t, 2H), 2.10 (m, 2H), 1.80 (m, 2H), 1.18 (t, 3H).

Example 4: 2-(4-fluorophenoxy)thiazole

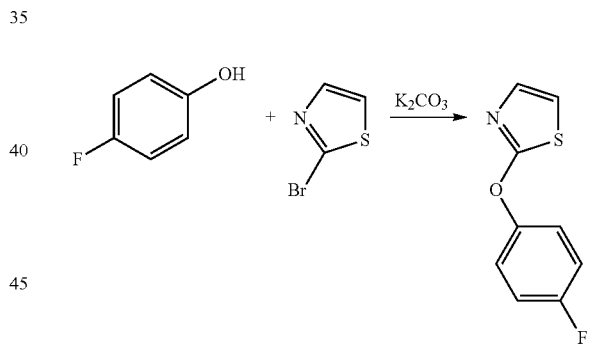

4-Fluorophenol (Sigma-Aldrich; 4.8 g, 43 mmol) and potassium carbonate (7.4 g, 54 mmol) were mixed in 20 ml anhydrous dimethylformamide, and the resulting slurry was stirred vigorously 5 h at 130° C. After allowing the reaction mixture to cool to 80° C., 2-bromothiazole (Sigma-Aldrich; 5.8 g, 36 mmol) in 5 ml dimethylformamide was added dropwise over 5 min, and the reaction mixture was heated 16 h at 130° C. After cooling to 25° C., 50 ml water was added, the reaction mixture was extracted with 3×50 ml ethyl acetate. The extracts were pooled and washed with 3×25 ml 6% NaOH, 25 ml water, and 25 ml brine, and were dried over anhydrous sodium sulfate and concentrated to a brown oil. The product was isolated via silica chromatography (ethyl acetate/hexanes gradient) on a CombiFlash Companion. Yield: 6.88 g (99%). $^1$H NMR (400 MHz, CDCl$_3$): δ 7.27 (m, 2H), 7.22 (d, 2H), 7.10 (d, 2H)

Example 5: 2-(4-fluorophenoxy)thiazole-5-carbaldehyde

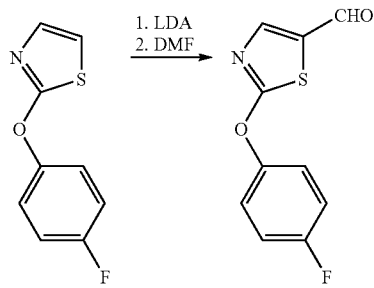 [SMILES: Fc1ccc(Oc2nccs2)cc1 ; "1. LDA2. DMF" ; O=Cc1cnc(Oc2ccc(F)cc2)s1]

Lithium diisopropylamide (LDA) was freshly prepared according to the following procedure: Diisopropylamine (8.1 mL; 57.83 mmol, Sigma-Aldrich) in 60 ml tetrahydrofuran was cooled to −78° C.; n-butyl-lithium (26.5 ml 2.0 M in cyclohexanes; 53 mmol; Sigma-Aldrich) was added drop-wise over 10 min. Stirring was continued for 5 min at 0° C., followed by re-cooling to −78° C. for 30 min. The formed LDA was cannulated into a solution of 2-(4-fluorophenoxy)thiazole (Example 4; 6.88 g; 35.3 mm) in 60 mL anhydrous tetrahydrofuran at −78° C. (dry ice bath) over 5 min. The reaction was stirred 30 min, 5.5 ml anhydrous dimethylformamide was added drop-wise over 5 min, and stirring was continued 10 min. The dry ice bath was removed, and the reaction mixture was stirred 10 min. The reaction was quenched with 50 ml saturated ammonium chloride and extracted with 3×50 ml ethyl acetate, and the pooled organic extracts were dried with brine and anhydrous sodium sulfate and evaporated to a brown solid. The product was isolated via silica chromatography (ethyl acetate/hexanes gradient) on a CombiFlash Companion. Yield: 4.7 g (60%).

$^1$H NMR (400 MHz, CDCl$_3$): δ 9.95 (s, 1H), 8.17 (s, 1H), 7.27 (d, 2H), 7.18 (d, 2H).

Example 6: Methyl (E)-6-(3-((E)-3-(2-(4-fluorophenoxy)thiazol-5-yl)-2-methylacryloyl)-4-hydroxy-2-oxo-2H-pyran-6-yl)hex-2-enoate

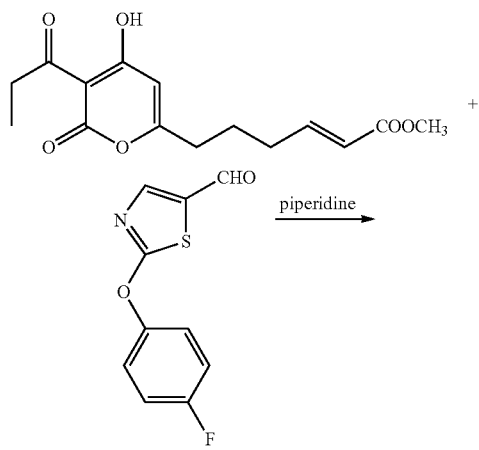

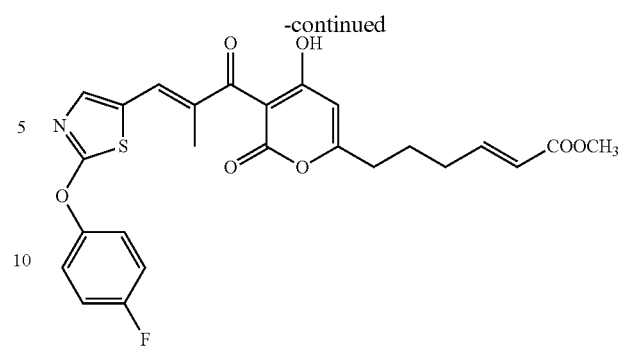

Methyl (E)-6-(4-hydroxy-2-oxo-3-propionyl-2H-pyran-6-yl)hex-2-enoate (Example 3; 346 mg; 1.18 mmol) and 2-(4-fluorophenoxy)thiazole-5-carbaldehyde (Example 5; 264 mg; 1.18 mmol) were mixed in 8 ml isopropanol in a sealed vial, warmed until solids went into solution, and allowed to cool to 25° C. Piperidine (116.6 μl, 1.18 mm; Sigma-Aldrich) was added, and the reaction mixture was heated 16 h at 70° C. with vigorous stirring. The reaction mixture was evaporated to an oil, re-dissolved in 10 ml dichloromethane, shaken vigorously with 25 ml 1 M HCl in a separatory funnel, and re-extracted with 2×50 ml dichloromethane. The combined dichloromethane extracts were washed with 25 ml water and 25 ml brine, dried over anhydrous sodium sulfate, and evaporated to an oil. The product was isolated via silica chromatography (ethyl acetate/hexanes gradient) on a CombiFlash Companion. Yield: 227 mg (38%). $^1$H NMR (500 MHz, CDCl$_3$): δ 7.37 (s, 1H), 7.29 (d, 2H), 7.13 (d, 2H), 7.03 (s, 1H), 6.90 (m, 1H), 5.97 (s, 1H), 5.81 (d, 1H), 3.72 (s, 3H), 2.54 (t, 2H), 2.30 (m, 2H), 2.13 (s, 3H), 1.88 (m, 2H). MS (MALDI): calculated: m/z 500.51 (MW); found: 500.11.

Example 7: (E)-6-(3-((E)-3-(2-(4-fluorophenoxy)thiazol-5-yl)-2-methyl acryl oyl)-4-hydroxy-2-oxo-2H-pyran-6-yl)hex-2-enoic acid

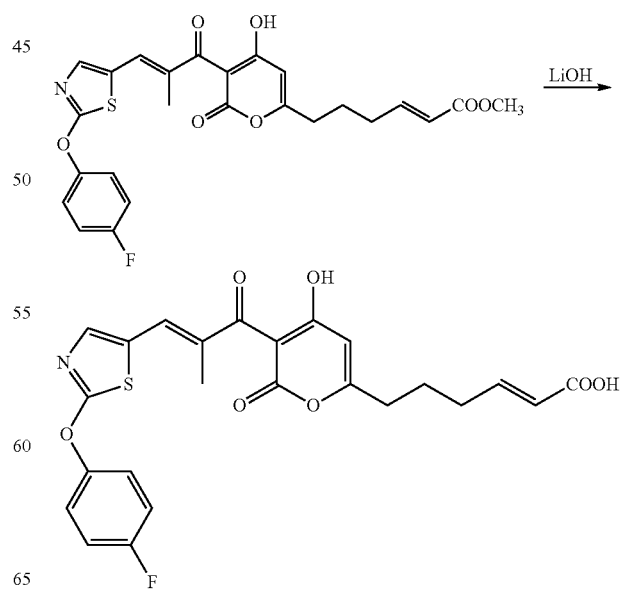

To methyl (E)-6-(3-((E)-3-(2-(4-fluorophenoxy)thiazol-5-yl)-2-methylacryloyl)-4-hydroxy-2-oxo-2H-pyran-6-yl)hex-2-enoate (Example 6; 150 mg; 0.300 mmol) in 13.2 ml t-butanol and 2.7 ml water, was added 1.65 ml 1M LiOH. The mixture was microwaved (Biotage Initiator; Biotage) 1 h at 60° C. Upon cooling to 25° C., the reaction mixture was evaporated to dryness, re-dissolved in 30 ml ethyl acetate and 20 ml 0.5 M HCl, adjusted to pH~2, and extracted with 3×20 ml ethyl acetate. The combined extracts were washed with brine, dried over anhydrous sodium sulfate, and evaporated to an oil. The product was isolated via silica chromatography (ethyl acetate/hexanes gradient) on a CombiFlash Companion. Yield: 0.133 g (90%). $^1$H NMR (500 MHz, CDCl$_3$): δ 7.37 (s, 1H), 7.29 (d, 2H), 7.13 (d, 2H), 7.03 (s, 1H), 6.90 (m, 1H), 5.97 (s, 1H), 5.81 (d, 1H), 2.54 (t, 2H), 2.30 (m, 2H), 2.13 (s, 3H), 1.88 (m, 2H). MS (MALDI): calculated: m/z 486.48 (MH$^+$); found: 486.11.

Example 8

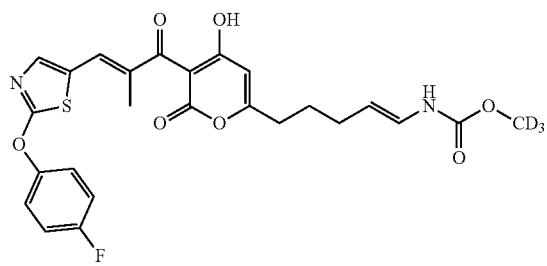 [SMILES: [2H]C([2H])([2H])OC(=O)N/C=C/CCCc1cc(O)c(C(=O)/C(C)=C/c2cnc(Oc3ccc(F)cc3)s2)c(=O)o1]

The title compound was obtained by conversion of (E)-6-(3-((E)-3-(2-(4-fluorophenoxy)thiazol-5-yl)-2-methylacryloyl)-4-hydroxy-2-oxo-2H-pyran-6-yl)hex-2-enoic acid (Example 7) into the acyl azide, followed by Curtius rearrangement under thermal conditions to yield the isocyanate, followed by addition of deuterated methanol. To (E)-6-(3-((E)-3-(2-(4-fluorophenoxy)thiazol-5-yl)-2-methylacryloyl)-4-hydroxy-2-oxo-2H-pyran-6-yl)hex-2-enoic acid (Example 7; 1.31 g, 2.63 mmol) and diisopropylamine (Sigma-Aldrich; 2.25 ml; 13 mmol) in anhydrous acetone (200 ml) under argon at 0° C., was added ethyl chloroformate (Sigma-Aldrich); 0.95 ml; 9.9 mmol), and the reaction mixture was stirred 1.5 h at 0° C. Sodium azide (1.7 g; 13 mmol) in 50 ml water was added, the reaction was stirred 45 min at 0° C., and the reaction was quenched by addition of 50 ml ice-water. The pH of the mixture was adjusted to ~2 by addition of 1 N HCl. Organics were extracted with 3×50 ml ethyl acetate, and the combined extracts were washed with 50 ml brine, dried over anhydrous sodium sulfate, evaporated to an oil, and trace water was removed by azeotropic evaporation of added anhydrous toluene azeotrope (3×30 ml). The crude azide was further dried 20 min under high vacuum, then re-dissolved in anhydrous toluene (140 ml) and heated 2 h at 110° C. The reaction mixture was allowed to cool to 80° C., and 70 ml anhydrous deuterated methanol (methanol-d4, 99.8 atom % D; Sigma-Aldrich) was added, and heating was continued for 12 h at 80° C. The reaction mixture was allowed to cool to room temperature, and evaporated to dryness. The product was isolated via silica chromatography (ethyl acetate/hexanes gradient) on a CombiFlash Companion. Deuterated methanol was recovered for future use by distillation. Yield: 0.984 g (70%). $^1$H NMR (500 MHz, CDCl$_3$): δ 7.36 (s, 1H), 7.27 (d, 2H), 7.15 (d, 2H), 7.11 (s, 1H), 6.51-6.43 (broad t, 1H), 6.25-6.17 (broad d, 1H), 5.97 (s, 1H), 4.99-4.88 (m, 1H), 2.51 (t, 2H), 2.13 (s, 3H), 2.05 (m, 2H), 1.75 (m, 2H). MS (MALDI): calculated: m/z 518.54 (MH$^+$); found: 518.17.

Example 9

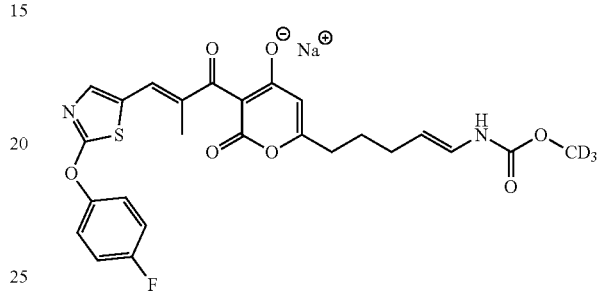

The compound of Example 8 (241 mg, 0.466 mmol) was suspended in 160 ml 50 mM sodium carbonate, and the suspension was stirred 3 h at 25° C. until all solids dissolved. Aliquots (32 ml each) of the resulting solution were applied to 10 g HF Mega BE-C18 reversed-phase cartridges (Agilent; prepared for use by one cycle of filling to rim with acetonitrile and draining and two cycles of filling to rim with water and draining), washed with 2×50 ml degassed water, and eluted with 5×20 ml 50% methanol, monitoring elution by monitoring yellow color. Pooled factions containing the title compound (first two 50% methanol fractions). were evaporated to yield a yellow crystalline solid. Yield: 210 mg (84%). $^1$H NMR (500 MHz, CD$_3$OD): δ 7.44 (s, 1H), 7.42 (s, 1H), 7.37 (d, 2H), 7.23 (d, 2H), 6.43 (d, 1H), 5.71 (s, 1H), 5.10 (m, 1H), 2.42 (t, 2H), 2.13 (m, 2H), 2.06 (s, 3H), 1.70 (m, 2H). MS (MALDI): calculated: m/z 540.54 (M+Na$^+$); found: 540.17.

Example 10

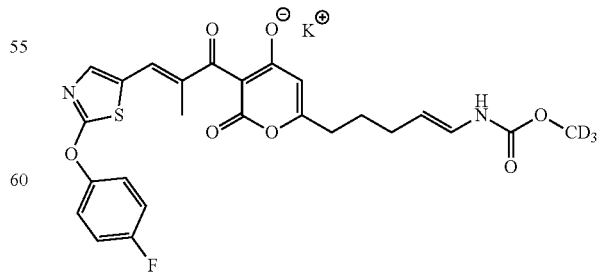

Example 10 was prepared analogously to Example 9, but using potassium carbonate in place of sodium carbonate.

Example 11

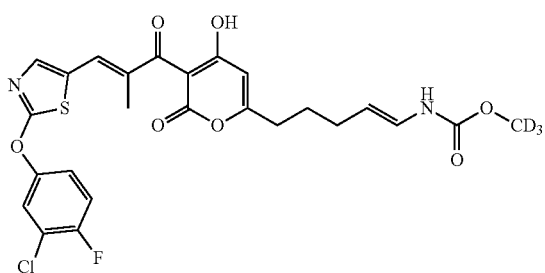 [SMILES: [2H]C([2H])([2H])OC(=O)N/C=C/CCCc1cc(O)c(C(=O)/C(C)=C/c2cnc(Oc3ccc(F)c(Cl)c3)s2)c(=O)o1]

Example 11 was prepared as described for Examples 4-8, but using 3-chloro-4-fluorophenol (Sigma-Aldrich) in place of 4-fluorophenol in the first reaction step. Yield (last reaction step): 47 mg (45%). $^1$H NMR (500 MHz, CDCl$_3$): δ 7.42 (br s, 1H), 7.34 (s, 1H), 7.15 (m, 2H), 7.02 (s, 1H), 6.51-6.43 (broad t, 1H), 6.25-6.17 (broad d, 1H), 5.97 (s, 1H), 4.99-4.88 (m, 1H), 2.51 (t, 2H), 2.13 (s, 3H), 2.05 (m, 2H), 1.75 (m, 2H). MS (MALDI): calculated: m/z 552.98 (MH$^+$); found: 551.99, 553.95.

Example 12

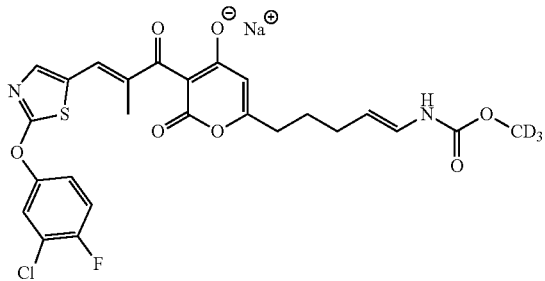 [SMILES: [2H]C([2H])([2H])OC(=O)N/C=C/CCCc1cc([O-])c(C(=O)/C(C)=C/c2cnc(Oc3ccc(F)c(Cl)c3)s2)c(=O)o1 ; [Na+]]

The compound of Example 11 (26 mg, 47 μmol) was suspended in 15 ml 50 mM sodium carbonate and stirred for 16 h at 25° C. The resulting solution was applied to a 10 g HF Mega BE-C18 reversed-phase cartridge (Agilent; prepared for use by one cycle of filling to rim with acetonitrile and draining and two cycles of filling to rim with water and draining), washed with 2×50 ml degassed water, and eluted with 10 ml 50% methanol, 10 ml 75% methanol, and 10 ml 80% methanol, monitoring elution by monitoring yellow color. Pooled factions containing the title compound (first two fractions) were evaporated to yield a yellow crystalline solid. Yield: 18 mg (67%).

Example 13

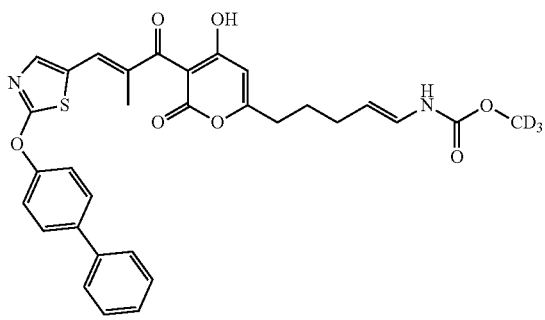 [SMILES: [2H]C([2H])([2H])OC(=O)N/C=C/CCCc1cc(O)c(C(=O)/C(C)=C/c2cnc(Oc3ccc(-c4ccccc4)cc3)s2)c(=O)o1]

Example 13 was prepared as described for Examples 4-8, but using 4-phenylphenol (Sigma-Aldrich) in place of 4-fluorophenol in the first reaction step. Yield (last reaction step): 82 mg (70%. $^1$H NMR (500 MHz, CDCl3): δ 7.66-7.25 (m, 9H), 7.34 (s, 1H), 7.05 (s, 1H), 6.51-6.43 (broad t, 1H), 6.25-6.17 (broad d, 1H), 5.97 (s, 1H), 4.99-4.88 (m, 1H), 2.51 (t, 2H), 2.13 (s, 3H), 2.05 (m, 2H), 1.75 (m, 2H). MS (MALDI): calculated: m/z 575.65 (M+H$^+$); found: 576.01, 597.99 (M+Na$^+$).

Example 14

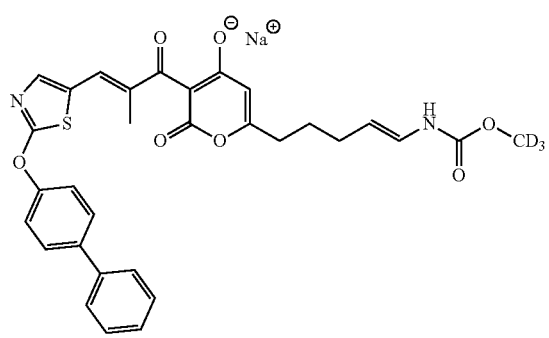 [SMILES: [2H]C([2H])([2H])OC(=O)N/C=C/CCCc1cc([O-])c(C(=O)/C(C)=C/c2cnc(Oc3ccc(-c4ccccc4)cc3)s2)c(=O)o1 ; [Na+]]

The compound of Example 13 (15 mg, 20 μmol) was suspended in 12 ml 50 mM sodium carbonate and stirred for 16 h at 25° C. The resulting solution was applied to a 10 g HF Mega BE-C18 reversed-phase cartridge (Agilent; prepared for use by one cycle of filling to rim with acetonitrile and draining and two cycles of filling to rim with water and draining), washed with 2×50 ml degassed water, and eluted with 10 ml 50% methanol, 10 ml 75% methanol, and 10 ml 80% methanol, monitoring elution by monitoring yellow color. Pooled factions containing the title compound (first two fractions) were evaporated to yield a yellow crystalline solid. Yield: 12 mg (58%).

Example 15: Assay of Solubility: Dilution from Organic Solvent into Aqueous Buffer Serial dilutions of test articles were prepared in dimethyl sulfoxide at 100× the final concentration. Test article solutions and blanks were diluted 100× into phosphate-buffered saline (PBS; 0.01 M sodium phosphate, pH 7.4, 137 mM NaCl, and 3 mM KCl) in a 96-well plate and mixed. After 2 h at 37° C., the presence of precipitate was detected by turbidity (absorbance at 540 nm). An absorbance value of greater than "mean+3×SD of the blank" (after subtracting background) was considered an indication of turbidity. The solubility limit was reported as the highest tested concentration with no evidence of turbidity. Data for representative compounds are provided in Table 1.

Example 16: Assay of Solubility; Dissolution in Aqueous Buffer in Absence of Organic Solvent Starting with 0.5-5 mg test compound in a glass vial at room temperature, successive cycles of addition of vehicle, vortexing 15 s, and inspection were performed until all test compound dissolved. Vehicles were: 0.01 M sodium phosphate (pH 7.4); 5% dextrose in 0.01 M sodium phosphate (pH 7.4); and 0.5% carboxymethylcellulose (CMC)/0.5% Tween-80 (pH 8.4). Data for representative compounds are provided in Table 2.

Example 17: Assay of Inhibition of Bacterial RNA Polymerase

Example 17.1: Assay of Inhibition of *Escherichia coli* RNA Polymerase

Fluorescence-detected RNA polymerase assays with *E. coli* RNA polymerase were performed by a modification of the procedure of Kuhlman et al., 2004 [Kuhlman, P., Duff, H. & Galant, A. (2004) A fluorescence-based assay for multisubunit DNA-dependent RNA polymerases. *Anal. Biochem.* 324, 183-190]. Reaction mixtures contained (20 µl): 0-100 nM test salt, 75 nM *E. coli* RNA polymerase $\sigma^{70}$ holoenzyme, 20 nM 384 bp DNA fragment containing the bacteriophage T4 N25 promoter, 100 µM ATP, 100 µM GTP, 100 µM UTP, 100 µM CTP, 50 mM Tris-HCl, pH 8.0, 100 mM KCl, 10 mM $MgCl_2$, 1 mM DTT, 10 µg/ml bovine serum albumin, and 5.5% glycerol. Reaction components other than DNA and NTPs were pre-incubated for 10 min at 37° C. Reactions were carried out by addition of DNA and incubation for 5 min at 37° C., followed by addition of NTPs and incubation for 60 min at 37° C. DNA was removed by addition of 1 µl 5 mM $CaCl_2$ and 2 U DNaseI (Ambion, Inc.), followed by incubation for 90 min at 37° C. RNA was quantified by addition of 100 µl RiboGreen RNA Quantitation Reagent (Invitrogen, Inc.; 1:500 dilution in Tris-HCl, pH 8.0, 1 mM EDTA), followed by incubation for 10 min at 25° C., followed by measurement of fluorescence intensity [excitation wavelength=485 nm and emission wavelength=535 nm; QuantaMaster QM1 spectrofluorometer (PTI, Inc.)]. IC50 is defined as the concentration of inhibitor resulting in 50% inhibition of RNA polymerase activity.

Example 17.2: Assay of Inhibition of *Mycobacterium tuberculosis* RNA Polymerase Fluorescence-detected RNA polymerase assays with *M. tuberculosis* RNA polymerase were performed as in Example 17.1, using reaction mixtures containing (20 µl): 0-100 nM test salt, 75 nM *M. tuberculosis* RNA polymerase core enzyme, 300 nM *M. tuberculosis* $\sigma^A$, 20 nM 384 bp DNA fragment containing the bacteriophage T4 N25 promoter, 100 µM ATP, 100 µM GTP, 100 UTP, 100 µM CTP, 40 mM Tris-HCl, pH 8.0, 80 mM NaCl, 5 mM $MgCl_2$, 2.5 mM DTT, and 12.7% glycerol. IC50 is defined as the concentration of inhibitor resulting in 50% inhibition of RNA polymerase activity.

Example 17.3: Assay of Inhibition of *Staphylococcus aureus* RNA Polymerase Fluorescence-detected RNA polymerase assays with *S. aureus* RNA polymerase were performed as in Example 17.1, using reaction mixtures containing (20 µl): 0-100 nM test salt, 75 nM *S. aureus* RNA polymerase core enzyme, 300 nM *S. aureus* $\sigma^A$, 20 nM 384 bp DNA fragment containing the bacteriophage T4 N25 promoter, 100 µM ATP, 100 µM GTP, 100 µM UTP, 100 CTP, 40 mM Tris-HCl, pH 8.0, 80 mM NaCl, 5 mM $MgCl_2$, 2.5 mM DTT, and 12.7% glycerol. IC50 is defined as the concentration of inhibitor resulting in 50% inhibition of RNA polymerase activity.

Data for representative compounds from the assays of Example 17 are provided in Table 3.

Example 18: Assay of Inhibition of Bacterial Growth in Culture

Example 18.1: Assay of Inhibition of Growth of *Staphylococcus aureus* and *Escherichia coli*

Minimum inhibitory concentrations (MICs) for *Staphylococcus aureus* ATCC 12600 and *Escherichia coli* D21f2tolC were quantified using spiral gradient endpoint assays, essentially as described [Wallace, A. and Corkill, J. (1989) Application of the spiral plating method to study antimicrobial action. *J. Microbiol. Meths.* 10, 303-310; Paton, J., Holt, A., and Bywater, M. (1990) Measurement of MICs of antibacterial agents by spiral gradient endpoint compared with conventional dilution methods. *Int. J. Exp. Clin. Chemother.* 3, 31-38; Schalkowsky S. (1994) Measures of susceptibility from a spiral gradient of drug concentrations. *Adv. Exp. Med. Biol.* 349, 107-120]. Assays employed exponential-gradient plates containing 150 mm×4 mm Mueller-Hinton II cation-adjusted agar and 0.4-100 µg/ml of test salt. Plates were prepared using an Autoplate 4000 spiral plater (Spiral Biotech, Inc.). Saturated overnight cultures were swabbed radially onto plates, and plates were incubated for 16 h at 37° C. For each culture, the streak length was measured using a clear plastic template (Spiral Biotech, Inc.), the test-salt concentration at the streak endpoint was calculated using the program SGE (Spiral Biotech, Inc.), and the MIC was defined as the calculated test-salt concentration at the streak endpoint.

Example 18.2: Assay of Inhibition of Growth of *Mycobacterium tuberculosis*

MICs for *Mycobacterium tuberculosis* H37Rv were quantified using microplate Alamar Blue assays as described [Collins, L. & Franzblau, S. (1997) Microplate Alamar Blue assay versus BACTEC 460 system for high-throughput screening of salts against *Mycobacterium tuberculosis* and *Mycobacterium avium*. *Antimicrob. Agents Chemother.* 41, 1004-1009].

Data for representative compounds from the assays of Example 18 are provided in Table 4.

Example 19. Assay of Antibacterial Efficacy in Mouse Model of *Staphylococcus aureus* Systemic Infection ("Peritonitis Model")

Female Swiss Webster mice (0.18-0.22 kg) were experimentally infected by intraperitoneal administration of $1\times10^7$ colony forming units of methicillin-resistant *Staphylococcus aureus* (MRSA) strain BAA-1707 (USA-400, MW2) in 5% hog gastric mucin. Test compounds in vehicle (5% dextrose in 10 mM sodium phosphate, pH 7.4), positive control in vehicle (linezolid at 12.5 mg/kg), and negative control (vehicle only), were administered by intravenous injection into a tail vein (200 µl) 0 h post-infection to provide single intravenous doses of 1.56, 3.125, 6.25, 12.5, 25, and 50 mg/kg or by oral gavage (400 µl) 1 h pre-infection to provide single oral doses of 3.125, 6.25, 12.5, 25, 50, and 100 mg/kg. Survival was monitored for 72 h post-infection. Identities of test salts and controls were blinded from personnel performing injections and monitoring survival. The effective dose 50 (ED50) was defined as the test-compound dose resulting in 50% survival at 72 h (calculated using the probit method).

Data for representative compounds from the assay of Example 19 are provided in Tables 5 and 6.

Example 20. Assay of Antibacterial Efficacy in Mouse Model of *Staphylococcus aureus* Lung Infection ("Neutropenic Pneumonia Model")

Female Swiss Webster mice (0.18-0.20 kg) were rendered immunosuppressed by oral gavage for 4 days with cyclophosphamide and were infected by intranasal administration of $1\times10^8$ colony forming units of methicillin-resistant *Staphylococcus aureus* (MRSA) strain BAA-1707 (USA-400, MW2). Test compounds in vehicle (5% dextrose in 10 mM sodium phosphate, pH 8.25), positive control in vehicle (vancomycin at 100 mg/kg), and negative control (vehicle only), were administered by intravenous injection into a tail vein (200 μl) 1 h post-infection to provide single intravenous doses of 25, 50, and 100 mg/kg or by oral gavage (200 μl) 1 h post-infection to provide oral doses of 100, 200, and 400 mg/kg. Mice were euthanized and lungs were harvested and homogenized 24 h post-infection; and viable bacteria were quantified. The effective dose (ED(2 log)) was defined as the minimum test-compound dose resulting in log reduction in bacterial burden.

Data for representative compounds from the assay of Example 20 are provided in Tables 7 and 8.

Example 21. Assay of Antibacterial Efficacy in Mouse Model of *Staphylococcus aureus* Dermal Infection ("Dermal-Infection Model")

Female BALB/c mice (0.18-0.20 kg) were experimentally infected by topical administration under isfluurane anesthesia of $1\times10^7$ colony forming units of methicillin-resistant *Staphylococcus aureus* (MRSA) strain BAA-1707 (USA-400, MW2) to a 20 mm×20 mm dorsal surface prepared by depilation (24 h pre-infection; isoflurane anesthesia) and removal of epidermis by tape stripping (immediately pre-infection; isoflurane anesthesia; seven applications and removals of 3M Nexcare surgical tape). Test compounds in vehicle (5% dextrose in 10 mM sodium phosphate, pH 8.25), positive control in vehicle (linezolid at 12.5 mg/kg), and negative control (vehicle only), were administered by intravenous injection into a tail vein (200 μl) 0 h post-infection to provide single intravenous doses of 12.5, 25, 50, and 100 mg/kg. Mice were euthanized and a 10 mm×10 mm skin segment was harvested and homogenized 24 h post-infection; and viable bacteria were quantified. Identities of test salts and controls were blinded from personnel performing injections and quantifying bacteria. The effective dose (ED(2 log)) was defined as the minimum test-compound dose resulting in log reduction in bacterial burden.

Data for representative compounds from the assay of Example 21 are provided in Table 9.

Example 22. Assay of Antibacterial Efficacy in Mouse Model of *Mycobacterium tuberculosis* Aerosol Acute Infection ("Mtb Acute Infection Model")

Female Balb/c mice (6-8 weeks old) were infected by aerosol administration of 50-100 colony forming units of *Mycobacterium tuberculosis* Erdman. Test compounds in vehicle (5% dextrose in 10 mM sodium phosphate, pH 8.25), positive control in vehicle (rifampi at 10 and 20 mg/kg), and negative control (vehicle only), were administered by oral gavage (200 μl) starting 7 days post-infection and continuing for 12 days to provide 12 daily oral doses of 100 and 200 mg/kg. Mice were euthanized and lungs and spleens were harvested and homogenized 21 days post-infection; and viable bacteria were quantified. The effective dose (ED(2 log)) was defined as the minimum test-compound dose resulting in log reduction in bacterial burden.

Data for representative compounds from the assay of Example 22 are provided in Table 10.

Screening data for representative salts of this invention (Example 9, Example 10, Example 12, and Example 14) and for the corresponding free acids (Example 8 and Example 11, and Example 13) are presented in Tables 1-10:

TABLE 1

Solubility: dilution from organic solvent into aqueous buffer.

| Compound | solubility (mg/ml) |
| --- | --- |
| Example 9 (salt) | ≥5 |
| Example 8 (free acid) | 0.1 |

TABLE 2

Solubility; dissolution in aqueous buffer in absence of organic solvent

| compound | solubility aqueous buffer, pH 7.4 (mg/ml) | solubility 5% dextrose in aqueous buffer, pH 7.4 (mg/ml) | solubility 0.5% CMC/0.5% Tween, pH 8.4 (mg/ml) |
| --- | --- | --- | --- |
| Example 9 (salt) | 10 | 5 | 20 |
| Example 8 (free acid) | <0.1 | <0.1 | <0.1 |

TABLE 3

Inhibition of bacterial RNA polymerase

| compound | RNAP-inhibitory activity *M. tuberculosis* RNAP IC50 (μM) | RNAP-inhibitory activity *S. aureus* RNAP IC50 (μM) | RNAP-inhibitory activity *E. coli* RNAP IC50 (μM) |
| --- | --- | --- | --- |
| Example 9 (salt) | 0.03 | 0.03 | 0.003 |
| Example 10 (salt) | | | 0.006 |
| Example 12 (salt) | 0.03 | 0.003 | 0.003 |
| Example 14 (salt) | >6 | 0.03 | 0.05 |
| Example 8 (free acid) | 0.02 | 0.06 | 0.004 |
| Example 11 (free acid) | 0.03 | 0.001 | 0.003 |
| Example 13 (free acid) | >6 | 0.01 | 0.02 |

TABLE 4

Inhibition of bacterial growth

| compound | in vitro antibacterial activity *M. tuberculosis* H37Rv MIC (μg/ml) | in vitro antibacterial activity *S. aureus* ATCC12600 MIC (μg/ml) | in vitro antibacterial activity *E. coli* D21f2tolC MIC (μg/ml) |
|---|---|---|---|
| Example 9 (salt) | 0.4 | 0.4 | 0.04 |
| Example 10 (salt) |  | 0.2 | 0.03 |
| Example 12 (salt) | 0.8 | 0.2 | 0.03 |
| Example 14 (salt) | >50 | >8 | 0.03 |
| Example 8 (free acid) | 0.8 | 0.3 | 0.06 |
| Example 11 (free acid) | 0.8 | 0.2 | 0.02 |
| Example 13 (free acid) | >50 | >8 | 0.03 |

TABLE 5

Antibacterial efficacy in mice: methicillin-resistant
*Staphylococcus aureus* (MRSA) peritonitis, intravenous
administration of test compound in 5% dextrose,
10 mM sodium phosphate, pH 7.4 (single dose).

| Compound | in vivo antibacterial activity: mouse MRSA peritonitis ED50 (mg/kg) |
|---|---|
| Example 9 (salt) | 10 |

TABLE 6

Antibacterial efficacy in mice: methicillin-resistant
Staphylococcus *aureus* (MRSA) peritonitis, oral administration
of test compound in in 5% dextrose, 10 mM sodium phosphate,
pH 7.4 (single dose).

| Compound | in vivo antibacterial activity: mouse MRSA peritonitis ED50 (mg/kg) |
|---|---|
| Example 9 (salt) | 10 |

TABLE 7

Antibacterial efficacy in mice: methicillin-resistant
*Staphylococcus aureus* (MRSA) lung infection, intravenous
administration of test compound in 5% dextrose,
10 mM sodium phosphate, pH 8.25 (single dose)

| Compound | in vivo antibacterial activity: mouse MRSA pneumonia ED(2 log) (mg/kg) |
|---|---|
| Example 9 (salt) | 25 |

TABLE 8

Antibacterial efficacy in mice: methicillin-resistant
*Staphylococcus aureus* (MRSA) lung infection, oral administration
of test compound in in 5% dextrose, 10 mM sodium phosphate, pH 7.4.

| Compound | in vivo antibacterial activity: mouse MRSA pneumonia ED(2 log) (mg/kg) |
|---|---|
| Example 9 (salt) | 100 |

TABLE 9

Antibacterial efficacy in mice: methicillin-resistant
*Staphylococcus aureus* (MRSA) dermal infection, intravenous
administration of test compound in in 5% dextrose,
10 mM sodium phosphate, pH 8.25 (single dose).

| Compound | in vivo antibacterial activity: mouse MRSA dermal infection ED(2 log) (mg/kg) |
|---|---|
| Example 9 (salt) | 10 |

TABLE 10

Antibacterial efficacy in mice: methicillin-resistant
*Mycobacterium tuberculosis* aerosol acute infection, oral administration
of test compound in in 5% dextrose, 10 mM sodium phosphate,
pH 8.25 (12 daily doses).

| Compound | in vivo antibacterial activity: mouse *Mycobacterium tuberculosis* aerosol acute infection ED(2 log) (mg/kg) |
|---|---|
| Example 9 (salt) | 200 |

The data in Table 1 show that a salt of this invention (EXAMPLE 9) is at least approximately 50 times more soluble than the corresponding free acid (Example 8) upon dilution from organic solvent into aqueous buffer.

The data in Table 2 show that a salt of this invention (EXAMPLE 9) is at least approximately 100 times more soluble than the corresponding free acid (Example 8) upon dissolution in aqueous buffer at pH 7.4 in the absence of organic solvent or surfactant.

The data in Table 2 further show that a salt of this invention (EXAMPLE 9) is at least approximately 50 times more soluble than the corresponding free acid (Example 8) upon dissolution in 5% dextrose in aqueous buffer at pH 7.4 in the absence of organic solvent.

The data in Table 2 further show that a salt of this invention (EXAMPLE 9) is at least approximately 200 times more soluble than the corresponding free acid (Example 8) upon dissolution in 0.5% CMC/0.5% Tween (pH 8.4) in the absence of organic solvent.

The data in Tables 1-2 show that a salt of this invention (EXAMPLE 9), unlike the corresponding free acid (Example 8), can be formulated at concentrations up to at least approximately 10 mg/ml in aqueous vehicles near neutral pH in the absence of organic solvent and at concentrations up to at least approximately 10 mg/ml in aqueous vehicles near neutral pH in the absence of both organic solvent and surfactant.

The data in Table 3 show that certain compounds of this invention potently inhibit bacterial RNA polymerases.

The data in Table 4 show that certain compounds of this invention potently inhibit the Gram-positive bacteria *Mycobacterium tuberculosis* and *Staphylococcus aureus*, and the Gram-negative bacterium *Escherichia coli*.

The data in Tables 5-10 indicate that certain compounds of this invention potently treat infections prevent death from bacterial infection in a mammal. Table 5 presents data for survival from experiments with mice with systemic infections of methicillin-resistant *Staphylococcus aureus* (MRSA) and compounds administered intravenously. Table 6 presents data for survival from experiments with mice with systemic infections of methicillin-resistant *Staphylococcus aureus* (MRSA) and compounds administered intravenously or orally.

The data in Tables 6-10 indicate that certain compounds of this invention potently treat infections and reduce bacterial burdens in a mammal. Tables 7 and 8 presents data for reductions in plasma bacterial burdens from experiments with mice with lung infections of methicillin-resistant *Staphylococcus aureus* (MRSA) and test compounds administered intravenously or orally. Table 9 presents data for reductions in bacterial burdens from experiments with mice with dermal infections of methicillin-resistant *Staphylococcus aureus* (MRSA) and compounds administered intravenously. Table 10 presents data for reductions in bacterial burdens from experiments with mice with aerosol acute infections of *Mycobacterium tuberculosis* and test compounds administered orally.

The data in Tables 5-10 further indicate that certain compounds of this invention can be administered to mammals intravenously at doses up to at least 100 mg/kg or orally at doses up to at least 400 mg/kg when formulated in an aqueous vehicle near neutral pH in the absence of both organic solvent and surfactant.

What is claimed is:

1. A composition comprising the salt of formula Ia:

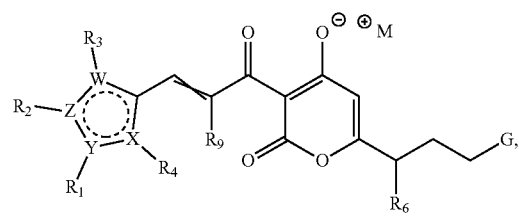

wherein:

W is sulfur oxygen, or nitrogen;

X, Y, and Z are individually carbon, sulfur, oxygen, or nitrogen, wherein at least two of X, Y, and Z are carbon;

one of $R^1$ and $R^2$ is $C_1$-$C_{10}$ alkyl, $C_2$-$C_{10}$ alkenyl, $C_1$-$C_{10}$ alkoxy, aryloxy, heteroaryloxy, or $NR^aR^b$, wherein any $C_1$-$C_{10}$ alkyl, $C_2$-$C_{10}$ alkenyl, or $C_1$-$C_{10}$ alkoxy, is optionally substituted by at least one of halogen, hydroxy, $C_1$-$C_5$ alkoxy, tetrahydrofuranyl, or furanyl, and wherein any aryloxy or heteroaryloxy is optionally substituted by at least one of halogen, hydroxy, $C_1$-$C_5$ alkyl, $C_1$-$C_5$ alkoxy, aryl, or heteroaryl, wherein any $C_1$-$C_5$ alkyl, $C_1$-$C_5$ alkoxy, aryl, and heteroaryl is optionally substituted by at least one of halogen, hydroxy, $C_1$-$C_5$ alkyl, or $C_1$-$C_5$ alkoxy; or one of $R^1$ and $R^2$ is a 5-6-membered saturated, partially unsaturated, or aromatic heterocycle that is optionally substituted by at least one of halogen, hydroxy, $C_1$-$C_{10}$ alkyl, $C_2$-$C_{10}$ alkenyl, or $C_1$-$C_{10}$ alkoxy; and the other of $R^1$ and $R^2$ is absent or is one of H, halogen, $C_1$-$C_{10}$ alkyl, $C_2$-$C_{10}$ alkenyl, or $C_1$-$C_{10}$ alkoxy, wherein any $C_1$-$C_{10}$ alkyl, $C_2$-$C_{10}$ alkenyl, or $C_1$-$C_{10}$ alkoxy is optionally substituted by at least one of halogen, hydroxy, or $C_1$-$C_5$ alkoxy;

$R^3$ is absent, or is one of H, $C_1$-$C_2$ alkyl, or halogen-substituted $C_1$-$C_2$ alkyl;

$R^4$ is absent, or is one of H, halogen, $C_1$-$C_2$ alkyl, or halogen-substituted $C_1$-$C_2$ alkyl;

$R^6$ is H, halogen, or methyl that optionally is substituted by halogen;

G is one of —CH=CH—NHC(O)—$R^7$, —CH=CH—NHC(S)—$R^7$, —CH$_2$CH$_2$NHC(O)—$R^7$, —CH$_2$CH$_2$NHC(S)—$R^7$, —CH$_2$NHNHC(O)—$R^7$, or —CH$_2$NHNHC(S)—$R^7$;

$R^7$ is one of $C_1$-$C_6$ alkyl, —O($C_1$-$C_6$ alkyl), —S($C_1$-$C_6$ alkyl), or —N($R^8$)$_2$, provided $R^7$ is not deuterated alkyl;

each $R^8$ is independently one of hydrogen or —$C_1$-$C_6$ alkyl;

$R^9$ is $C_1$-$C_{10}$ alkyl or $C_2$-$C_{10}$ alkenyl, wherein any $C_1$-$C_{10}$ alkyl or $C_2$-$C_{10}$ alkenyl is optionally substituted by at least one of halogen, hydroxy, alkoxy, or $NR^aR^b$;

each $R^a$ is $C_1$-$C_{10}$ alkyl that is optionally substituted by at least one of halogen, hydroxy, or $C_1$-$C_5$ alkoxy;

each $R^b$ is H or $C_1$-$C_{10}$ alkyl that is optionally substituted by at least one of halogen, hydroxy, or $C_1$-$C_5$ alkoxy; and $M^+$ is a pharmaceutically acceptable cation; and water, wherein the composition is substantially co-solvent free, substantially surfactant free, and has a pH of from about 7 to about 9, and wherein the concentration of the salt is at least about 0.25 mg/mL.

2. The salt:

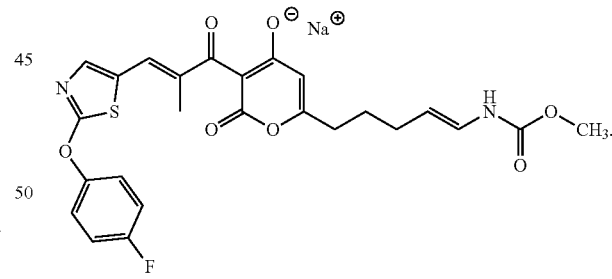

3. A composition comprising the salt of claim 2 and water, wherein the composition is substantially co-solvent free, substantially surfactant free, and has a pH of from about 7 to about 9, and wherein the concentration of the salt is at least about 0.25 mg/mL.

* * * * *